US012668649B2

(12) United States Patent
Roussel et al.

(10) Patent No.: US 12,668,649 B2
(45) Date of Patent: Jun. 30, 2026

(54) MONOGLYCEROL ACRYLATE BASED POLYMER AND USES THEREOF

(71) Applicant: Université LAVAL, Québec (CA)

(72) Inventors: Sabrina Roussel, Québec (CA); Nicolas Bertrand, Québec (CA); Philippe Grenier, Québec (CA)

(73) Assignee: Université Laval, Quebec. (CA)

( * ) Notice: Subject to any disclaimer, the term of this patent is extended or adjusted under 35 U.S.C. 154(b) by 357 days.

(21) Appl. No.: 18/367,542

(22) Filed: Sep. 13, 2023

(65) Prior Publication Data

US 2024/0101733 A1 Mar. 28, 2024

(30) Foreign Application Priority Data

Sep. 13, 2022 (CA) ................................ CA 3172967

(51) Int. Cl.
*C08F 120/12* (2006.01)
*A61K 9/1273* (2025.01)
*C08L 91/00* (2006.01)

(52) U.S. Cl.
CPC .......... *C08F 120/12* (2013.01); *A61K 9/1273* (2013.01); *C08L 91/00* (2013.01)

(58) Field of Classification Search
CPC ..................................................... C08F 120/12
See application file for complete search history.

(56) References Cited

U.S. PATENT DOCUMENTS

| | | | |
|---|---|---|---|
| 10,086,077 | B2 | 10/2018 | Kim et al. |
| 2004/0241855 | A1 | 12/2004 | Cullis et al. |
| 2017/0100316 | A1 | 4/2017 | Dickhof et al. |

FOREIGN PATENT DOCUMENTS

| | | | |
|---|---|---|---|
| CA | 2709875 | | 7/2019 |
| EP | 2700708 | A2 | 2/2014 |
| EP | 2217269 | B1 | 4/2017 |
| FR | 2678830 | B1 | 3/1995 |
| WO | WO/2015/085318 | | 6/2015 |
| WO | WO/2020/061457 | | 3/2020 |

OTHER PUBLICATIONS

Allen, T. M. et al. (1991) "Liposomes containing synthetic lipid derivatives of poly(ethylene glycol) show prolonged circulation half-lives in vivo," Biochimica et Biophysica Acta (BBA)—Biomembranes 1066(1), 29-36 published Jul. 1, 1991.
Bangham, A. D. et al. (1967) "Osmotic properties and water permeability of phospholipid liquid crystals," Chemistry and Physics of Lipids 1(3), 225-246 published May 1, 1967.
Bertrand, N. et al. (2010) "Transmembrane pH-Gradient Liposomes To Treat Cardiovascular Drug Intoxication," ACS Nano 4(12), 7552-7558 published Dec. 28, 2010.
Emeny, R. T. et al. (2007) "B1-Adrenergic Receptors on Immune Cells Impair Innate Defenses against Listeria," The Journal of Immunology 178(8), 4876-4884.
Farokhzad, O. C. et al. (2006) "Targeted nanoparticle-aptamer bioconjugates for cancer chemotherapy in vivo," Proceedings of the National Academy of Sciences 103(16), 6315-6320.
Frey, H. et al. (2002) "Dendritic polyglycerol: a new versatile biocompatible material," Reviews in Molecular Biotechnology 90(3), 257-267 published May 1, 2002.
Gref, R. et al. (1994) "Biodegradable Long-Circulating Polymeric Nanospheres," Science 263(5153), 1600-1603.
Hope, M. J. et al. (1985) "Production of large unilamellar vesicles by a rapid extrusion procedure. Characterization of size distribution, trapped vol. and ability to maintain a membrane potential," Biochimica et Biophysica Acta (BBA)—Biomembranes 812(1), 55-65 published Jan. 10.
Janzen, J. et al. (1996) "Interfacial thickness of liposomes containing poly(ethylene glycol)-cholesterol from electrophoresis," Biophysical Journal 70(1), 313-320 published Jan. 1, 1996.
Li, Y. et al. (2023) "Biomimetic nanoparticles targeting atherosclerosis for diagnosis and therapy," Smart Medicine 2(3), e20230015.
You, D. G. et al. (2014) "Dextran sulfate-coated superparamagnetic iron oxide nanoparticles as a contrast agent for atherosclerosis imaging," Carbohydrate Polymers 101, 1225-1233 published Jan. 30, 2014.
Cunningham VJ, AM Alswieleh, KL Thompson, M Williams, GJ Leggett, SP Armes, and OM Musa (2014). Poly (glycerol monomethacrylate)-poly(benzyl methacrylate) diblock copolymer nanoparticles via RAFT emulsion polymerization: synthesis, characterization, and interfacial activity. Macromolecules 47: 5613-5623.
Chen Y, D Diaz-Dussan, Y-Y Peng, and R Narain (2019). Hydroxyl-rich PGMA-based cationic glycopolymers for intracellular siRNA delivery: biocompatibility and effect of sugar decoration degree. Biomacromolecules 20: 2068-2074.
Violante de Paz M and R Grosso (2021). Polymeric materials for the development of dual-working gastroretentive drug delivery systems. A breakthrough approach. Academ J Polym Sci 4: AJOP.MS. ID.555646.
Çağdaş M, AD Sezer, and S Bucak (2014). Liposomes as potential drug carrier systems for drug delivery. IntechOpen.
Rideau E, R Dimova, P Schwille, FR Wurm, and K Landfester (2018). Liposomes and polymersomes: a comparative review towards cell mimicking. Chem Soc Rev 47: 8572-8610.
Alavi M and M Hamidi (2019). Passive and active targeting in cancer therapy by liposomes and lipid nanoparticles. Drug Metab Pers Ther 34: 20180032.
Beltrán-Gracia E, A López-Camacho, I Higuera-Ciapara, JB Velázquez-Fernández, and AA Vallejo-Cardona (2019). Nanomedicine review: clinical developments in liposomal applications. Cancer Nano 10: 11.
Mohamed M, AS Abu Lila, T Shimizu, E Alaaeldin, A Hussein, HA Sarhan, J Szebeni, and T Ishida (2019). PEGylated liposomes: immunological responses. Sci Technol Adv Mater 20: 1 710-1724.

(Continued)

*Primary Examiner* — Genevieve S Alley
(74) *Attorney, Agent, or Firm* — Medlen & Carroll, LLP

(57) ABSTRACT

The present document relates to amphiphilic poly(monoglycerol acrylate) (PMGA) polymers, comprising an hydrophilic repeating unit of monoglycerol acrylate and one or more biodegradable hydrophobic group and their use and methods of use in the delivery of bioactive agents. Additionally, the invention provides a method for preparing monoglycerol acrylate-based polymers.

20 Claims, 21 Drawing Sheets

(56) References Cited

OTHER PUBLICATIONS

Nosova AS, OO Koloskova, AA Nikonova, VA Simonova, VV Smirnov, D Kudlay, and MR Khaitova (2019). Diversity of PEGylation methods of liposomes and their influence on RNA delivery. Med Chem Commun 10: 369.
Nunes SS, RS Fernandes, CH Cavalcante, I da Costa César, EA Leite, SCA Lopes, A Ferretti, D Rubello, DM Townsend, MC de Oliveira, VN Cardoso, ALB de Barros (2019). Influence of PEG coating on the biodistribution and tumor accumulation of pH-sensitive liposomes. Drug Deliv Transl Res 9: 123-130.
De Leo V, F Milano, A Agostiano, and L Catucci (2021). Recent advancements in polymer/liposome assembly for drug delivery: from surface modifications to hybrid vesicles. Polymers 13: 1027.
Igyártó BZ, S Jacobsen, and S Ndeupen (2021). Future considerations for the mRNA-lipid nanoparticle vaccine platform. Curr Opin Virol 48: 65-72.
Nakhaei P, R Margiana, DO Bokov, WK Abdelbasset, MA Jadidi Kouhbanani, RS Varma, F Marofi, M Jarahian, and N Beheshtkhoo (2021). Liposomes: structure, biomedical applications, and stability parameters with emphasis on cholesterol. Front Bioeng Biotechnol 9: 705886.
Tenchov R, R Bird, AE Curtze, and Q Zhou (2021). Lipid nanoparticles—From liposomes to mRNA vaccine delivery, a landscape of research diversity and advancement. ACS Nano 15: 16982-17015.
Fang Y, J Xue, S Gao, A Lu, D Yang, H Jiang, Y He, and K Shi (2017). Cleavable PEGylation: a strategy for overcoming the "PEG dilemma" in efficient drug delivery. Drug Deliv 24(sup1): 22-32.
Hoang Thi TT, EH Pilkington, DH Nguyen, J S Lee, K Dong Park, and NP Truong (2020). The importance of poly (ethylene glycol) alternatives for overcoming PEG immunogenicity in drug delivery and bioconjugation. Polymers 12: 298.
Kalyanram P, A Puri, and A Gupta (2020). Understanding the stealth properties of PEGylated lipids: a mini-review. Int J Lipids 1: 1-20.
Mohamed M, E Alaaeldin, A Hussein, and HA Sarhan (2020). Liposomes and PEGylated liposomes as drug delivery systems. J Adv Biomed Pharm Sci 3: 80-88.
Pilkington EH, EJA Suys, NL Trevaskis, AK Wheatley, D Zukancic, A Algarni , H Al-Wassiti , TP Davis, CW Pouton, SJ Kent, and NP Truong (2021). From influenza to COVID-19: lipid nanoparticle mRNA vaccines at the frontiers of infectious diseases. Acta Biomater 131: 16-40.
Ju Y, WS Lee, EH Pilkington, HG Kelly, S Li, KJ Selva, KM Wragg, K Subbarao, THO Nguyen, LC Rowntree, LF Allen, K Bond, DA Williamson, NP Truong, M Plebanski, K Kedzierska, S Mahanty, AW Chung, F Caruso, AK Wheatley, JA Juno, and SJ Kent (2022). Anti-PEG antibodies boosted in humans by SARS-CoV-2 lipid nanoparticle mRNA vaccine. ACS Nano 2022, 16, 8, 11769-11780. Published Jun. 27, 2022.
Moad G, E Rizzardo, and SH Thang (2012). Living radical polymerization by the RAFT process—A third update. Aust J Chem 65: 985-1076.
Semsarilar M and V Abetz (2021). Polymerizations by RAFT: developments of the technique and its application in the synthesis of tailored (co)polymers. Macromol Chem Phys 222: 2000311.
Hunter SJ, NJW Penfold, ER Jones, T Zinn, OO Mykhaylyk, and Steven P. Armes (2022). Synthesis of thermoresponsive diblock copolymer nano-objects via RAFT aqueous emulsion polymerization of hydroxybutyl methacrylate. Macromolecules 55: 3051-3062.
Chinthamanipeta PS, S Kobukata, H Nakata, and DA Shipp (2008). Synthesis of poly(methyl methacrylate)-silica nanocomposites using methacrylate-functionalized silica nanoparticles and RAFT polymerization. Polymer 49: 5636-5642.
Koler A and P Krajnc (2021). Surface modification of hypercrosslinked vinylbenzyl chloride polyHIPEs by grafting via RAFT. Macromol Chem Phys 222: 2000381.
Moad G, E Rizzardo, and SH Thang (2010). Reversible addition fragmentation chain transfer (RAFT) polymerization. Mater Matters 5(1): 2-8.
Yu X, M-T Picker, M Schneider, A Herberg, S Pascual, L Fontaine, D Kuckling, D (2018). Synthesis of amphiphilic block copolymers based on SKA by RAFT polymerization. Macromol Chem Phys 219: 1700506.
Bonnotte B, M Gough, V Phan, A Ahmed, H Chong, F Martin, and RG Vile (2003). Intradermal injection, as opposed to subcutaneous injection, enhances immunogenicity and suppresses tumorigenicity of tumor cells. Cancer Res 63: 2145-2149.
Hickling JK, KR Jones, M Friede, D Zehrung, D Chen, and D Kristensen (2011). Intradermal delivery of vaccines: potential benefits and current challenges. Bull World Health Organ 89: 221-226.
Weniger BG and MJ Papania (2013). Alternative vaccine delivery methods [Chapter 61]. In: Plotkin SA, WA Orenstein, and PA Offit, eds. Vaccines, 6th ed., Elsevier/Saunders, Philadelphia, pp. 1200-1231.
Saitoh A and Y Aizawa (2016). Intradermal vaccination for infants and children. Hum Vaccin Immunother 12: 2447-2455.
Yu DM, DM Smith, H Kim, J Rzayev, and TP Russell (2019). Two-step chemical transformation of polystyrene-block-poly(solketal acrylate) copolymers for increasing x. Macromolecules 52: 6458-6466.
Truong NP, GR Jones, KGE Bradford, D Konkolewicz, and A Anastasaki (2021). A comparison of RAFT and ATRP methods for controlled radical polymerization. Nat Rev Chem 5: 859-869.
Teijaro JR and DL Farber (2021). COVID-19 vaccines: modes of immune activation and future challenges. Nat. Rev. Immunol. 21: 195-197.
Wagner, V.; Dullaart, A.; Bock, A.-K.; Zweck, A., The emerging nanomedicine landscape. Nature Biotechnology 2006, 24 (10), 1211-1217.
Lasic, D.; Papahadjopoulos, D., Liposomes revisited. Science 1995, 267 (5202), 1275-1276.
Kulkarni, J. A.; Darjuan, M. M.; Mercer, J. E.; Chen, S.; van der Meel, R.; Thewalt, J. L.; Tam, Y. Y. C.; Cullis, P. R., On the Formation and Morphology of Lipid Nanoparticles Containing Ionizable Cationic Lipids and siRNA. ACS Nano 2018, 12 (5), 4787-4795.
Cěh, B.; Winterhalter, M.; Frederik, P. M.; Vallner, J. J.; Lasic, D. D., Stealth® liposomes: from theory to product. Advanced Drug Delivery Reviews 1997, 24 (2), 165-177.
Senior, J.; Delgado, C.; Fisher, D.; Tilcock, C.; Gregoriadis, G., Influence of surface hydrophilicity of liposomes on their interaction with plasma protein and clearance from the circulation: Studies with poly(ethylene glycol)-coated vesicles. Biochimica et Biophysica Acta (BBA)—Biomembranes 1991, 1062 (1), 77-82.
Sharma, A.; Sharma, U. S., Liposomes in drug delivery: Progress and limitations. International Journal of Pharmaceutics 1997, 154 (2), 123-140.
Song, L. Y.; Ahkong, Q. F.; Rong, Q.; Wang, Z.; Ansell, S.; Hope, M. J.; Mui, B., Characterization of the inhibitory effect of PEG-lipid conjugates on the intracellular delivery of plasmid and antisense DNA mediated by cationic lipid liposomes. Biochimica et Biophysica Acta (BBA)—Biomembranes 2002, 1558 (1), 1-13.
Mui, B. L.; Tam, Y. K.; Jayaraman, M.; Ansell, S. M.; Du, X.; Tam, Y. Y. C.; Lin, P. J.; Chen, S.; Narayanannair, J. K.; Rajeev, K. G.; Manoharan, M.; Akinc, A.; Maier, M. A.; Cullis, P.; Madden, T. D.; Hope, M. J., Influence of Polyethylene Glycol Lipid Desorption Rates on Pharmacokinetics and Pharmacodynamics of siRNA Lipid Nanoparticles. Mol Ther Nucleic Acids 2013, 2 (12), e139-e139.
Mahmoudi, M.; Bertrand, N.; Zope, H.; Farokhzad, O. C., Emerging understanding of the protein corona at the nano-bio interfaces. Nano Today 2016, 11 (6), 817-832.
Dams, E. T. M .; Laverman, P.; Oyen, W. J. G.; Storm, G.; Scherphof, G. L.; Van der Meer, J. W. M.; Corstens, F. H. M.; Boerman, O. C., Accelerated blood clearance and altered biodistribution of repeated injections of sterically stabilized liposomes. J Pharm Exp Ther 2000, 292 (3), 1071-9.
Ishida, T.; Ichihara, M.; Wang, X.; Yamamoto, K.; Kimura, J.; Majima, E.; Kiwada, H., Injection of PEGylated liposomes in rats

(56) References Cited

OTHER PUBLICATIONS elicits PEG-specific IgM, which is responsible for rapid elimination of a second dose of PEGylated liposomes. Journal of Controlled Release 2006, 112 (1), 15-25.
Grenier, P.; Viana, I. M. d. O.; Lima, E. M.; Bertrand, N., Anti-polyethylene glycol antibodies alter the protein corona deposited on nanoparticles and the physiological pathways regulating their fate in vivo. Journal of Controlled Release 2018, 287, 121-131.
Judge, A.; Mcclintock, K.; Phelps, J. R.; MacLachlan, I., Hypersensitivity and Loss of Disease Site Targeting Caused by Antibody Responses to PEGylated Liposomes. Molecular Therapy 2006, 13 (2), 328-337.
Sellaturay, P.; Nasser, S.; Ewan, P., Polyethylene Glycol-Induced Systemic Allergic Reactions (Anaphylaxis). The Journal of Allergy and Clinical Immunology: In Practice 2021, 9 (2), 670-675.
Yang, Q.; Jacobs, T. M.; McCallen, J. D.; Moore, D. T.; Huckaby, J. T.; Edelstein, J. N.; Lai, S. K., Analysis of Pre- existing IgG and IgM Antibodies against Polyethylene Glycol (PEG) in the General Population. Analytical Chemistry 2016, 88 (23), 11804-11812.
Zhang, L.; Chan, J. M.; Gu, F. X.; Rhee, J.-W.; Wang, A. Z.; Radovic-Moreno, A. F.; Alexis, F.; Langer, R.; Farokhzad, O. C., Self-Assembled Lipid-Polymer Hybrid Nanoparticles: A Robust Drug Delivery Platform. ACS Nano 2008, 2 (8), 1696-1702.
Roux, E.; Passirani, C.; Scheffold, S.; Benoit, J.- P.; Leroux, J.-C., Serum-stable and long-circulating, PEGylated, pH-sensitive liposomes. Journal of Controlled Release 2004, 94 (2), 447-451.
Fairbanks, B. D.; Gunatillake, P. A.; Meagher, L., Biomedical applications of polymers derived by reversible addition—fragmentation chain-transfer (RAFT). Advanced Drug Delivery Reviews 2015, 91, 141-152.
Willcock, H.; O'Reilly, R. K., End group removal and modification of RAFT polymers. Polymer Chemistry 2010, 1 (2), 149-157.
Kitano, H.; Akatsuka, Y.; Ise, N., pH-responsive liposomes which contain amphiphiles prepared by using lipophilic radical initiator. Macromolecules 1991, 24 (1), 42-46.
Oguchi, K.; Sanui, K.; Ogata, N.; Takahashi, Y.; Nakada, T., Relationship between electron sensitivity and chemical structures of polymers as electron beam resist. VII: Electron sensitivity of vinyl polymers containing pendant 1,3-dioxolan groups. Polymer Engineering & Science 1990, 30 (8), 449-452.
Rossi, N. A. A.; Zou, Y.; Scott, M. D.; Kizhakkedathu, J. N., RAFT Synthesis of Acrylic Copolymers Containing Poly (ethylene glycol) and Dioxolane Functional Groups: Toward Well-Defined Aldehyde Containing Copolymers for Bioconjugation. Macromolecules 2008, 41 (14), 5272-5282.
Sousa, S. C. O.; Junior, C. G. L.; Silva, F. P. L.; Andrade, N. G.; Barbosa, T. P.; Vasconcellos, M. L. A. A., Microwave-promoted morita-baylis-hillman reactions: efficient synthesis of new monoacylglycerols (MAGs) as potential anti-parasitic compounds. Journal of the Brazilian Chemical Society 2011, 22, 1634-1643.
Das, B.; Banerjee, J.; Chowdhury, N.; Majhi, A., Synthetic Applications of Baylis–Hillman Chemistry: An Efficient and Solely Stereoselective Synthesis of (<i>E</i>)-α-Methylcinnamic Acids and Potent Hypolipidemic Agent LK-903 from Unmodified Baylis Hillman Adducts. Chemical and Pharmaceutical Bulletin 2006, 54 (12), 1725-1727.
Chen, M.; Moad, G.; Rizzardo, E., Thiocarbonylthio end group removal from RAFT-synthesized polymers by a radical-induced process. Journal of Polymer Science Part A: Polymer Chemistry 2009, 47 (23), 6704-6714.
Bertrand, N. S., Pierre; Leroux, Jean-Christophe Serum-Stable, Long-Circulating, pH-Sensitive PEGylated Liposomes. In: D'Souza G. (eds), liposomes: methods and protocols. New York, 2017; vol. 1522, p. 559.
Chotard, É.; Mohammadi, F.; Julien, P.; Berthiaume, L.; Rudkowska, I.; Bertrand, N., Drinkable lecithin nanovesicles to study the biological effects of individual hydrophobic macronutrients and food preferences. Food Chemistry 2020, 126736.
Bartlett, G. R., Phosphorus assay in column chromatography. The Journal of biological chemistry 1959, 234 (3), 466-468.
Greenspan, P.; Fowler, S. D., Spectrofluorometric studies of the lipid probe, nile red. J Lipid Res 1985, 26 (7), 781-9.
Li, Z.; Jia, L.; Wang, J.; Wu, X.; Hao, H.; Wu, Y.; Xu, H.; Wang, Z.; Shi, G.; Lu, C.; Shen, Y., Discovery of diamine- linked 17-aroylamido-17-demethoxygeldanamycins as potent Hsp90 inhibitors. European Journal of Medicinal Chemistry 2014, 87, 346-363.
Coutinho, P. J. G.; Castanheira, E. M. S.; Céu Rei, M.; Real Oliveira, M. E. C. D., Nile Red and DCM Fluorescence Anisotropy Studies in C12E7/DPPC Mixed Systems. The Journal of Physical Chemistry B 2002, 106 (49), 12841-12846.
Viana, I. M. d. O.; Grenier, P.; Defrêne, J.; Barabe, F.; Lima, E. M.; Bertrand, N., Role of the complement cascade in the biological fate of liposomes in rodents. Nanoscale 2020, 12 (36), 18875-18884.
Bertrand, N.; Fleischer, J. G.; Wasan, K. M.; Leroux, J.-C., Pharmacokinetics and biodistribution of N-isopropylacrylamide copolymers for the design of pH-sensitive liposomes. Biomaterials 2009, 30 (13), 2598-2605.
Perrier, S., 50th Anniversary Perspective: RAFT Polymerization—A User Guide. Macromolecules 2017, 50 (19), 7433-7447.
Dommanget, C.; D'Agosto, F.; Monteil, V., Polymerization of Ethylene through Reversible Addition-Fragmentation Chain Transfer (RAFT). Angewandte Chemie International Edition 2014, 53 (26), 6683-6686.
Thomas, D. B.; Convertine, A. J.; Hester, R. D.; Lowe, A. B.; McCormick, C. L., Hydrolytic Susceptibility of Dithioester Chain Transfer Agents and Implications in Aqueous RAFT Polymerizations. Macromolecules 2004, 37 (5), 1735-1741.
Chang, C.-W.; Bays, E.; Tao, L.; Alconcel, S. N. S.; Maynard, H. D., Differences in cytotoxicity of poly(PEGA)s synthesized by reversible addition-fragmentation chain transfer polymerization. Chemical Communications 2009, (24), 3580-3582.
Shen, W.; Chang, Y.; Liu, G.; Wang, H.; Cao, A.; An, Z., Biocompatible, Antifouling, and Thermosensitive Core-Shell Nanogels Synthesized by RAFT Aqueous Dispersion Polymerization. Macromolecules 2011, 44 (8), 2524-2530.
Trucillo, P.; Campardelli, R.; Reverchon, E., Liposomes: From Bangham to Supercritical Fluids. Processes 2020, 8 (9), 1022.
Ruysschaert, T.; Marque, A.; Duteyrat, J.-L.; Lesieur, S.; Winterhalter, M.; Fournier, D., Liposome retention in size exclusion chromatography. BMC Biotechnology 2005, 5 (1), 11.
Dikpati, A.; Mohammadi, F.; Greffard, K.; Queant, C.; Arnaud, P.; Bastiat, G.; Rudkowska, I.; Bertrand, N., Residual Solvents in Nanomedicine and Lipid-Based Drug Delivery Systems: a Case Study to Better Understand Processes. Pharmaceutical Research 2020, 37 (8), 149.
Grabielle-Madelmont, C.; Lesieur, S.; Ollivon, M., Characterization of loaded liposomes by size exclusion chromatography. Journal of Biochemical and Biophysical Methods 2003, 56 (1), 189-217.
Leroux, J.-C.; , Roux, E.; Le Garrec, D.; Hong, K.; Drummond, D. C., N-isopropylacrylamide copolymers for the preparation of pH-sensitive liposomes and polymeric micelles. Journal of Controlled Release 2001, 72 (1), 71-84.
Lee, S.-H.; Sato, Y.; Hyodo, M.; Harashima, H., Size-Dependency of the Surface Ligand Density of Liposomes Prepared by Post-insertion. Biological and Pharmaceutical Bulletin 2017, 40 (7), 1002-1009.
Lin, M.; Qi, X.-R., Purification Method of Drug-Loaded Liposome. In Liposome-Based Drug Delivery Systems, Lu, W.-L.; Qi, X.-R., Eds. Springer Berlin Heidelberg: Berlin, Heidelberg, 2018; pp. 1-11.
Ricker, R. D.; Sandoval, L. A., Fast, reproducible size-exclusion chromatography of biological macromolecules. Journal of Chromatography A 1996, 743 (1), 43-50.
Owen, S. C.; Chan, D. P. Y.; Shoichet, M. S., Polymeric micelle stability. Nano Today 2012, 7 (1), 53-65.
Gaucher, G.; Dufresne, M.-H.; Sant, V. P.; Kang, N.; Maysinger, D.; Leroux, J.-C., Block copolymer micelles: preparation, characterization and application in drug delivery. Journal of Controlled Release 2005, 109 (1), 169-188.
Biondi, A. C.; Féliz, M. R .; Disalvo, E. A., Surface changes induced by osmotic stress and its influence on the glycerol permeability in lipid bilayers. Biochimica et Biophysica Acta (BBA)—Biomembranes 1991, 1069 (1), 5-13.

(56) References Cited

OTHER PUBLICATIONS

Biswas, S. K.; Mantovani, A., Macrophage plasticity and interaction with lymphocyte subsets: cancer as a paradigm. Nat Immunol 2010, 11 (10), 889-96.
Wang, W.; Li, J.; Wu, K.; Azhati, B.; Rexiati, M., Culture and Identification of Mouse Bone Marrow-Derived Dendritic Cells and Their Capability to Induce T Lymphocyte Proliferation. Med Sci Monit 2016, 22, 244-50.
Copland, M. J.; Baird, M. A.; Rades, T.; Mckenzie, J. L.; Becker, B.; Reck, F.; Tyler, P. C.; Davies, N. M., Liposomal delivery of antigen to human dendritic cells. Vaccine 2003, 21 (9-10), 883-90.
Demel, R. A.; De Kruyff, B., The function of sterols in membranes. Biochimica et Biophysica Acta (BBA)—Reviews on Biomembranes 1976, 457 (2), 109-132.
Corvera, E.; Mouritsen, O. G.; Singer, M. A.; Zuckermann, M. J., The permeability and the effect of acyl-chain length for phospholipid bilayers containing cholesterol: theory and experiment. Biochimica et Biophysica Acta (BBA)—Biomembranes 1992, 1107 (2), 261-270.
Senior, J.; Gregoriadis, G., Stability of small unilamellar liposomes in serum and clearance from the circulation: The effect of the phospholipid and cholesterol components. Life Sciences 1982, 30 (24), 2123-2136.
Patel, H. M.; Tużel, N. S.; Ryman, B. E., Inhibitory effect of cholesterol on the uptake of liposomes by liver and spleen. Biochimica et Biophysica Acta (BBA)—General Subjects 1983, 761 (2), 142-151.
Wu, H.; Yu, M.; Miao, Y.; He, S.; Dai, Z.; Song, W.; Liu, Y.; Song, S.; Ahmad, E.; Wang, D.; Gan, Y., Cholesterol-tuned liposomal membrane rigidity directs tumor penetration and anti-tumor effect. Acta Pharmaceutica Sinica B 2019, 9 (4), 858-870.
Reddy, S. T.; van der Vlies, A. J.; Simeoni, E.; Angeli, V.; Randolph, G. J.; O'Neil, C. P.; Lee, L. K.; Swartz, M. A.; Hubbell, J. A., Exploiting lymphatic transport and complement activation in nanoparticle vaccines. Nature Biotechnology 2007, 25 (10), 1159-1164.
Oussoren, C.; Storm, G., Liposomes to target the lymphatics by subcutaneous administration. Advanced Drug Delivery Reviews 2001, 50 (1), 143-156.
De Oliveira Viana, I. M.; Roussel, S.; Defrêne, J.; Lima, E. M.; Barabé, F.; Bertrand, N., Innate and adaptive immune responses toward nanomedicines. Acta Pharmaceutica Sinica B 2021.
Mosmann, T., Rapid colorimetric assay for cellular growth and survival: Application to proliferation and cytotoxicity assays. Journal of Immunological Methods 1983, 65 (1), 55-63.
Justin B. Lee et al. (2011) Lipid nanoparticle siRNA systems for silencing the androgen receptor in human prostate cancer in vivo. International Journal of Cancer 131(5) E781.
Ambegia et al. (2005) Stabilized plasmid-lipid particles containing PEG-diacylglycerols exhibit extended circulation lifetimes and tumor selective gene expression. 1669 (2) 155.
Rizvi, Syed AA, and Ayman M. Saleh. "Applications of nanoparticle systems in drug delivery technology." Saudi pharmaceutical journal 26.1 (2018): 64-70.
Silva, Joana, et al. "Application of Nanotechnology in Drug Delivery." InTech eBooks, 2014, https://doi.org/10.5772/58424.

RAW 264.7 macrophage (mouse)
Cellular uptake (%)
100
80
60
40
20
0
0.25
1.00

Bone narrow derivated dentritic cells (mouse)
Cellular uptake (%)
80
60
40
20
0
1
2
5
10

A-20 immortalized B cells (mouse)
Cellular uptake (%)
20
15
10
5
0
0.5
1.0
5.0

U87-MG human glioblastoma ( human)
Cellular uptake (%)
40
30
20
10
0
0.1
1.0
Control liposome
Liposome PMGA-DODA
Quantity of material (ug)

MONOGLYCEROL ACRYLATE BASED POLYMER AND USES THEREOF

RELATED APPLICATION

This application claims priority from CA 3,172, 967 filed Sep. 13, 2022 which is herein incorporated by reference in its entirety.

TECHNICAL FIELD

The present disclosure relates to polymers, especially monoglycerol acrylate-based polymers, lipid particles comprising monoglycerol acrylate-based polymers and their use and methods of use in the delivery of bioactive agents. Additionally, the invention provides a method for preparing monoglycerol acrylate-based polymers.

BACKGROUND

The interest toward nanoparticles used for drug delivery has considerably grown in the last decade. As the technologies evolved, modalities expanded beyond the delivery of small molecules, towards proteins, peptides, monoclonal antibodies, and nucleic acids. The success of mRNA vaccines to control the COVID-19 pandemic have confirmed the huge potential of these technologies to impact human health. Nevertheless, despite these clinical successes, the technologies still face some challenges, and the next generation of nanomedicines will require improved stability and increased intracellular delivery. The widespread use of lipid nanoparticles (LNP) has also highlighted some limitations of the common ingredients used for their preparation. These systems are typically stabilized with polyethylene glycol (PEG); however, the use of this polymer has been shown to reduce interactions with the target cells. The polymer also raised some considerations regarding its immunogenicity. Indeed, studies revealed that the PEG can induce an immune response caused by anti-PEG antibodies and/or an accelerated blood clearance due to prior exposure to pharmaceuticals or other consumption products PEG-containing. It has been reported that anti-PEG antibodies could circulate in 25-72% of subjects (*J. Adv. Biomed. Pharm. Sci.,* 2020, 3, 80-88). Moreover, it has been recently shown that both mRNA vaccines against COVID-19 significantly boost the anti-PEG IgM response after vaccination in humans, thus increasing the importance to look for alternatives to PEG (*ACS Nano,* 2022, 16, 11769-11780).

Accordingly, there is a need for the development of alternative polymers that could be used in the preparation of lipid particles.

SUMMARY

According to one aspect, the present technology relates to monoglycerol acrylate-based polymers and their use in the composition of lipid particles. More specifically, the following embodiments are provided:

In one aspect, the present description provides an amphiphilic poly(monoglycerol acrylate) (PMGA) polymer, comprising
- an hydrophilic repeating unit of monoglycerol acrylate; and
- one or more biodegradable hydrophobic group;
- wherein the polymer is a comb polymer having an average molecular weight (Mw) ranging between 1000 and 15000, ranging between 1800 and 12000, of about 1800, of about 6500, or of about 12000; and
- wherein the Mw of the at least one biodegradable hydrophobic group represents at least 5%, at least 10%, at least 30%, between 5% and 30%, between 10% and 30%, about 5%, about 10% or about 30% of the average total Mw of the polymer.

In one aspect, the present description provides an amphiphilic PMGA polymer, wherein the PMGA polymer is of Formula (I):

Formula I

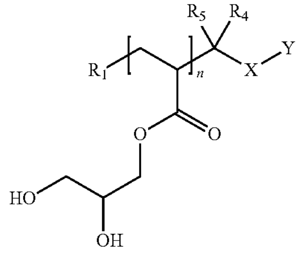

wherein,
- wherein n is an integer between 10 and 80, between 30 and 50, between 40 and 50, or about 42;
- X is $—(CH_2)_m—$ with m between 0 and 4;
- $R_1$ is a donor group or $R_1$ is halogen, —H, —OH, —SH, $—S(C{=}S)S—C_{6-10}$aryl, $—S(C{=}S)S—C_{1-24}$ alkyl, $—S(C{=}S)C_{1-24}$alkyl, —S(C=S)Ph;
- Y is —OH, —COOH, $—OR_6$, $—COO(CH_2)_LNR_2R_3$ or $—CONR_2R_3$ with L between 1 and 18;
- $R_2$ and $R_3$ are each independently —H, $C_{6-10}$ aryl, $C_{3-12}$ cycloalkyl, steroidyl groups,
- $C_{3-24}$ alkyl, $C_{3-24}$ alkenyl or $C_{3-24}$ alkynyl; and
- $R_4$ and $R_5$ are each independently —H, $—CH_3$ or —CN;
- $R_6$ is $(CH_2)_{L'}CH_3$, $(CH_2)_{L'}NR_2R_3$ with L' between 0 and 18 or $R_6$ is $(CH_2)_{L'}NR_2R_3$ with L' between 1 and 18.

In one aspect, the present description provides a method of preparing an amphiphilic PMGA polymer as defined herein, said method comprising:
- providing a monoglycerol acrylate monomer, radically polymerizable monomer;
- providing a chain transfer agent; and
- polymerizing the monomer via reversible addition-fragmentation chain-transfer polymerization (RAFT), in the presence of a free radical initiator and the chain transfer agent,
- wherein said polymerization is carried out in conditions allowing to obtain a polymer incorporating at least 10 monomer units (n).

In one aspect, the present description provides a polymer obtained by the method as defined herein.

In one aspect, the present description provides a lipid particle comprising the amphiphilic PMGA polymer as defined herein.

In one aspect, the present description provides a lipid particle, wherein the lipid particle comprises:
- a ionizable lipid;
- a phosphatidyl choline;
- a sterol; and
- an amphiphilic PMGA polymer as defined herein.

In one aspect, the present description provides a polymer as defined herein, for preparing a lipid particle.

In one aspect, the present description provides a pharmaceutical composition comprising a lipid particle as defined herein, and a pharmaceutically acceptable excipient, carrier, or diluent.

In one aspect, the present description provides a vaccine composition comprising a lipid particle as defined herein, and a pharmaceutically acceptable excipient, carrier, or diluent.

Additional objects and features of the present polymers, compositions, methods and uses will become more apparent upon reading of the following non-restrictive description of exemplary embodiments and examples section, which should not be interpreted as limiting the scope of the invention.

BRIEF DESCRIPTION OF THE FIGURES

FIG. 4A RAW 264.7 macrophages. FIG. 4B Dendritic cells derivate from bone narrow. FIG. 4C A-20 immortalized B cells. FIG. 4D U87 MG human's glioblastoma cells.

FIG. 10A Gating in spleen. FIG. 10B Gating in lymph node.

DETAILED DESCRIPTION

Definitions

Figure 1B:
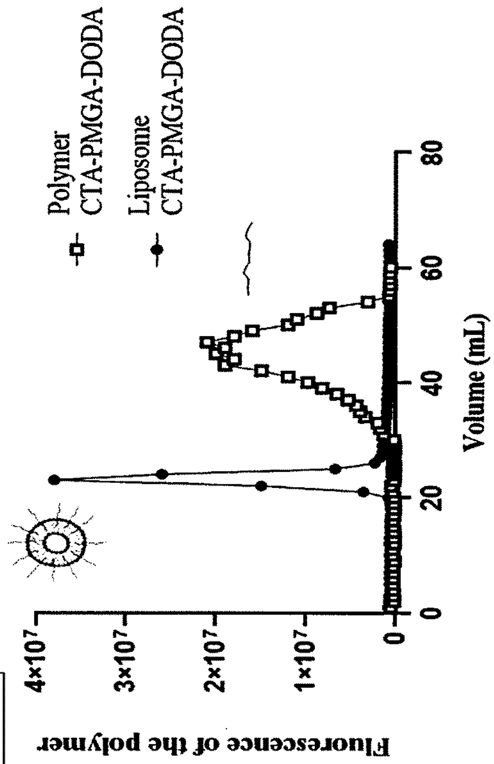
FIGS. 1A and 1B show the incorporation of the polymer into liposomes. Specifically, Size Exclusion Chromatography (SEC) shows that the polymer incorporates into liposomes, in which case limited free polymer is detectable. The free polymer is delayed/retained by a Sepharose CL-4B column (2×50 cm), but is excluded from the column when loaded as part of a liposome formulation (FIGS. 1A and 1B represent data obtained with PGMA-DODA and CTA-PMGA-DODA, respectively).

All technical and scientific terms and expressions used herein have the same definitions as those commonly understood by a person skilled in the art to which the present technology pertains. The definition of some terms and expressions used is nevertheless provided below. To the extent the definitions of terms in the publications, patents, and patent applications incorporated herein by reference are contrary to the definitions set forth in this specification, the definitions in this specification will control. The section headings used herein are for organizational purposes only and are not to be construed as limiting the subject matter disclosed.

Chemical structures described herein are drawn according to conventional standards. Also, when an atom, such as a carbon atom, as drawn seems to include an incomplete valency, then the valency is assumed to be satisfied by one or more hydrogen atoms even though these are not necessarily explicitly drawn. Hydrogen atoms should be inferred to be part of the compound.

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the context clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless otherwise stated, structures depicted herein are also meant to include all isomeric (e.g., enantiomeric, diastereomeric, tautomeric and geometric (or conformational) forms of the structure when applicable; for example, the R and S configurations for each asymmetric center. Therefore, single stereochemical isomers as well as enantiomeric, diastereomeric, tautomeric and geometric (or conformational) mixtures of the present compounds are within the scope of the present description. The present compounds unless otherwise noted, also encompasses all possible tautomeric forms of the illustrated compound, if any. The term also includes isotopically labeled compounds where one or more atoms have an atomic mass different from the atomic mass most abundantly found in nature. Examples of isotopes that may be incorporated into the present compounds include, but are not limited to, $^{2}H$ (D), $^{3}H$ (T), $^{11}C$, $^{13}C$, $^{14}C$, $^{15}N$, $^{18}O$, $^{17}O$, any one of the isotopes of sulfur, etc. The compounds may also exist in unsolvated forms as well as solvated forms, including hydrated forms. The compounds may exist in multiple crystalline or amorphous forms. In general, all physical forms are equivalent for the uses contemplated herein and are intended to be within the scope of the present invention.

The number of carbon atoms in a hydrocarbon substituent can be indicated by the prefix "$C_x$-$C_y$" or "$C_{x-y}$" where x is the minimum and y is the maximum number of carbon atoms in the substituent.

The term "alkyl" as used herein, refers to a saturated, straight- or branched-chain hydrocarbon radical typically containing from 1 to 24 carbon atoms. For example, "$C_{1-8}$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 24 carbon atoms. For example, "$C_{2-8}$alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 24 carbon atoms. For example, "$C_{2-8}$alkynyl" contains from two to eight carbon atoms. Representative alkynyl groups include, but are not limited to, for example, ethynyl, 1-propynyl, 1-butynyl, heptynyl, octynyl and the like.

The term "aryl" used alone or as part of a larger moiety as in "aralkyl", "aralkoxy", "aryloxy", or "aryloxyalkyl", refers to aromatic groups having 4n+2 conjugated π(pi) electrons, wherein n is an integer from 1 to 3, in a monocyclic moiety or a bicyclic or tricyclic fused ring system having a total of six to 15 ring members, wherein at least one ring in the system is aromatic and wherein each ring in the system contains three to seven ring members. The term "aryl" may be used interchangeably with the expression "aryl ring". In certain embodiments of the present description, "aryl" refers to an aromatic ring or ring system which includes, but is not limited to, phenyl, biphenyl, naphthyl, azulenyl, anthracyl and the like, which may bear one or more substituents. The term "aralkyl" or "arylalkyl" refers to an alkyl residue attached to an aryl ring. Examples of aralkyl include, but are not limited to, benzyl, phenethyl, and the like. Also included within the scope of the term "aryl", as it is used herein, is a group in which an aromatic ring is fused to one or more non-aromatic rings, such as indanyl, indenyl, phthalimidyl, naphthimidyl, fluorenyl, phenanthridinyl, or tetrahydronaphthyl, and the like. The term "$C_{6-n}$aryl" refers to an aryl group having from 6 to the indicated "n" number of atoms in the ring structure.

The term "donor group" refers to a substituent that can donate some of its electron density to neighboring atoms, usually by resonance or inductive effects. Examples of donor groups include but are not limited to: $-CH_3$, $-OR_a$, $-NR_aR_b$, $-SR_a$ and $-PR_aR_b$. $R_a$ and $R_b$ represent independently H or alkyl chains having at least one carbon atom.

The term hydrophobic group used herein refers to a moiety which is covalently attached via a suitable linker to the hydrophilic repeating unit of monoglycerol acrylate and permits anchoring into the lipid membrane of a lipid particles. Suitable hydrophobic groups includes alkyl, alkenyl or alkynyl chains having 3 to 24, 6 to 24, 12 to 24, 18 to 24 carbons, saturated or unsaturated, fatty acids having 6 to 24, 6 to 24, 12 to 24, 18 to 24 carbons in the aliphatic group and which can be linear or branched, (e.g., (iso)lauric, (iso) myristic, (iso)palmitic, or(iso)stearic acid, lauroleic, physeteric, myristoleic, palmitoleic, petroselinic, or oleic acid), and sterols.

The term "biodegradable" refers a group that that can be degraded under physiological conditions, for example, by means of hydrolysis or via an enzymatic reaction. In one aspect, when a biodegradable hydrophobic group is incorporated into a polymer according to the invention, this means that the polymer when administered to a subject such as a human disappears from the body over time.

As used herein, "physiological conditions" refers to conditions present in an organism including a human. For example, a pH of about 7.4 and a temperature of about 37° C.

The expression reversible addition-fragmentation chain-transfer (RAFT) refers to a synthetic method allowing the preparation of synthetic polymers via a mechanism of radical polymerization. The method of polymerization RAFT as used herein involves the polymerization of monomer units by addition-fragmentation and chain-transfer. Such method can provide complex polymer structures, such as copolymers, star-polymers and branched-polymers, including but not limited to comb-polymers. The RAFT polymerization experimental conditions involve a RAFT agent, also known as chain-transfer agent, a radical source, a monomer and a solvent.

The term chain transfer agent (CTA) or RAFT agent refers to the reagent used in the RAFT polymerization reaction. The CTA is used in RAFT polymerization to control the average molecular weight of the final polymer. The CTA is involved in a chain transfer reaction as it has a least one weak chemical bond which facilitates the chain transfer. Chain transfer agents can comprise, but are not limited to, compounds having dithioester or thiocarbonylthio groups.

PMGA Based Polymers

The present invention relates to amphiphilic poly(monoglycerol acrylate) (PMGA) polymers ("PMGA based polymers"). The PMGA based polymers comprise a hydrophilic repeating unit of monoglycerol acrylate and one or more biodegradable hydrophobic group as defined herein.

The amphiphilic properties of the PMGA based polymers allow them to be formulated as lipid particles such as lipid nanoparticles or liposomes. In one aspect, when formulated with lipid particles such as lipid nanoparticles or liposomes, the polymers of the present description allow for stabilization of the lipid particles while improving cellular targeting and uptake.

In one aspect, there is provided a PMGA polymer of Formula (I):

Formula I

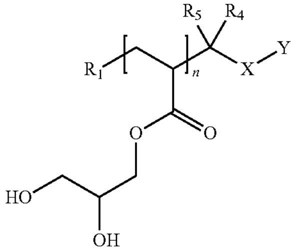

wherein the following embodiments are present alone or in combination:

wherein n is an integer between 10 and 80, between 30 and 50, between 40 and 50, or about 42;

X is $—(CH_2)_m—$ with m between 0 and 4; m is an integer between 0 and 2 or m is 0;

$R_1$ a donor group or $R_1$ is halogen, —H, —OH, —SH, $—S(C{=}S)S—C_{6-10}$aryl, $—S(C{=}S)S—C_{1-24}$alkyl, $—S(C{=}S)C_{1-24}$alkyl, —S(C=S)Ph; or $R_1$ is halogen, —H, —OH, —SH, $—S(C{=}S)S—C_{6-10}$aryl, $—S(C{=}S)S—C_{1-24}$alkyl; or $R_1$ is —OH, —SH, or $—S(C{=}S)S—C_{1-24}$alkyl;

Y is —OH, —COOH, $—OR_6$, $—COO(CH_2)_LNR_2R_3$ or $—CONR_2R_3$ with L between 1 and 18; or Y is —OH, —COOH, $—OR_6$, $—COO(CH_2)_LNR_2R_3$ or $—CONR_2R_3$ with L between 1 and 18; or Y is —OH or $—CONR_2R_3$; or Y is $CONR_2R_3$;

$R_2$ and $R_3$ are each independently —H, $C_{6-10}$ aryl, $C_{3-12}$ cycloalkyl, steroidyl groups, $C_{3-24}$ alkyl, $C_{3-24}$ alkenyl or $C_{3-24}$ alkynyl; or $R_2$ and $R_3$ are each independently $—C_{3-24}$ alkyl;

$R_4$ and $R_5$ are each independently —H, $—CH_3$ or —CN; and $R_6$ is $(CH_2)_{L'}CH_3$, $(CH_2)_{L'}NR_2R_3$ with L' between 0 and 18 or $R_6$ is $(CH_2)_{L'}CH_3$, $(CH_2)_{L'}NR_2R_3$ with L' between 0 and 6 or $R_6$ is $(CH_2)_{L'}NR_2R_3$ with L' between 1 and 6.

In a further aspect, the following embodiments are present alone or in combination $R_2$ and $R_3$ are each independently linear $C_{6-24}$ alkyl. $R_2$ and $R_3$ are both $C_{18}H_{37}$.

$R_1$ is halogen, —H, —OH, —SH, $—S(C{=}S)S—C_{6-10}$ aryl, $—S(C{=}S)S—C_{1-24}$ alkyl. $R_1$ is halogen, —H, —OH or —SH. $R_1$ is $—S(C{=}S)S—C_{10-24}$alkyl. $R_1$—SH.

n is comprised between 30 and 50. n is 42.

$R_4$ is $—CH_3$.

$R_5$ is —CN.

X is $—CH_2CH_2—$.

Y is $—CONR_2R_3$.

In one aspect, there is provided a PMGA polymer of Formula (I):

Formula I

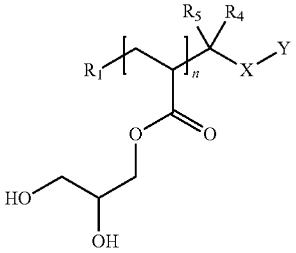

wherein n is an integer between 40 and 50, or about 42;

X is $—(CH_2)_m—$ with m being 2;

$R_1$ is SH, or $—S(C{=}S)S—C_{10-16}$alkyl;

Y is -is $CONR_2R_3$, $R_2$ and $R_3$ are each independently $—C_{3-24}$ alkyl or $C_{6-24}$ alkyl or $C_{18-24}$ alkyl; and $R_4$ and $R_5$ are each independently —H, $—CH_3$ or —CN provided that one of $R_4$ and $R_5$ is $CH_3$ or —CN; or $R_4$ is —CN and $R_5$ is $CH_3$.

In one aspect, there is provided a PMGA polymer of Formula (I):

Formula I

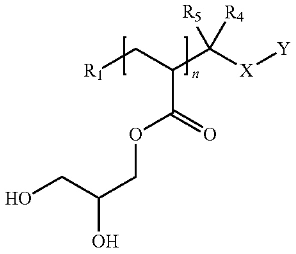

wherein n is about 42;

X is $—(CH_2)_m—$ with m being 2;

$R_1$ is SH, or $—S(C{=}S)S—C_{10-14}$alkyl;

Y is -is $CONR_2R_3$;

$R_2$ and $R_3$ are each independently $—C_{18}$alkyl; and $R_4$ is —CN and $R_5$ is $CH_3$.

Synthesis and Characterization of Polymers

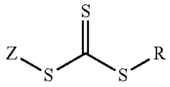

Trithiocarbonate CTA

-continued

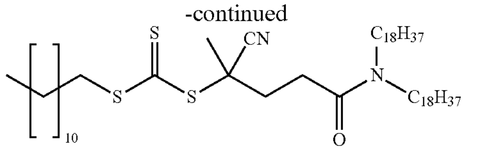

DODA-CTA

To allow anchoring of the poly(mocoglycerol acrylate) or PMGA to liposomes irrespective of the presence of the Z dodecyl-moiety, we conjugated dioctadecylamine (DODA) to the R-group of a trithiocarbonate chain transfer agent (CTA). Trithiocarbonate CTA are less active than dithioesters as transfer agents but still allow a good control over the polymerization of acrylates. Also, trithiocarbonate CTA give less retardation, are less prone to hydrolytic degradation and more readily synthesized.

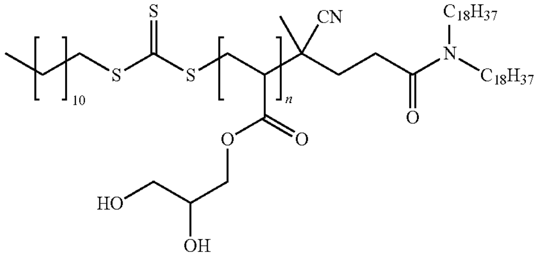

CTA-PMGA-DODA

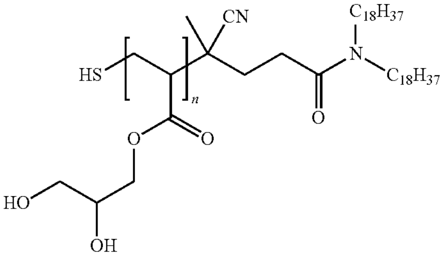

PMGA-DODA

The CTA-PMGA-DODA polymer synthesized with the DODA-CTA contains three alkyl chains, two 18-carbon tails on the R-group (dioctadecylamine) and one dodecyl moiety on the Z-group (12 carbons). In theory, both hydrophobic segments can contribute to the polymolecular assemblies and can act as anchoring points on the lipid bilayer. However, it has been shown that longer alkyls chains remain associated with the membrane longer in biological samples due to more energy required for them to leave the bilayer. Also, CTAs with dodecyl Z-groups are sulfur analogs designed to rapidly undergo radical homolysis between the thiocarbonylthio function and the polymer. The bond created between those is normally weak enough to be prone to hydrolysis. Hydrolytic susceptibility is accelerated by the increase of temperature and pH. In *Chemical Communications* 2009, (24), 3580-3582, was reported substantial cytotoxicity in vitro due to the hydrolytic release of the RAFT moiety (dithiocarbonate). The authors observed no cytotoxicity with the trithiocarbonate function since they are more stable and resistant to hydrolysis. However, in *Macromolecules* 2011, 44 (8), 2524-2530 was demonstrated later that trithiocarbonate functions can also have apparent toxicities. They suggest that trithiocarbonate end groups attached to linear polymers are more susceptible to hydrolysis than those attached on non-linear polymer due to steric effects. While toxicity arguments support the removal of the Z-group before in vitro and in vivo experiments, we also conducted experiments with the presence of an alkylated Z-group to evaluate its influence on the stability of liposomes (CTA-PMGA-DODA polymer). The CTA-PMGA-DODA polymer can be submitted to hydrolysis using a mixture of two radical initiators, such has lauroyl peroxide (LPO) and azobisisobutironitrile (AIBN) (2:20 molar equivalent to the polymer) to afford the PMGA-DODA polymer with the thiol end group.

The molecular weight of the CTA-PMGA-DODA polymer was determined by $^1$H-NMR by integrating the signal of the $CH_3$ at the end of the alkyl chain (0.9 ppm). The polydispersity index ($M_w/M_n$) was also evaluated by size exclusion chromatography analysis (SEC) using a Polysep-GFC P-3000 with 70% methanol in water, a mobile phase that disrupted the intermolecular interactions between the polymers. The $M_w/M_n$ was around 1.30 and the molecular weight was 5904 g/mol (n=41). Reversible addition fragmentation chain-transfer (RAFT) polymerization was conducted with a CTA/initiator ratio ([CTA]/[I]) of 10, classic conditions for RAFT are 70° C. with a pressure under 200 bars and in the absence of oxygen as reported in *Angewandte Chemie International Edition* 2014, 53 (26), 6683-6686.

Preparation and Characterization of Liposome and Stability of the Carrier

One of the most common approaches used to prepare liposomes is the thin film hydration method also known as the Bangham method. This method relies on the spontaneous rearrangement of dried lipids into spherical vesicles in water as described in *Processes* 2020, 8 (9), 1022. These relatively large multilamellar vesicles are further extruded through polycarbonate membranes to form smaller monodisperse unilamellar vesicles. Here, this process allowed preparing liposomes with and without PMGA (CTA-PMGA-DODA or PMGA-DODA) with a diameter of around 100 nm, as measured by Dynamic Light Scattering (DLS).

To monitor the incorporation of the polymer into the liposomes, a fluorescent polymer was synthesized by incorporating 1 mol % of acrylic acid (AA) to the synthesis and conjugating carboxylic functions to amino-terminated fluorescein cadaverin. The molecular weight of this polymer was characterized by $^1$H-NMR to obtain 5616 g/mol (n=39). Size exclusion chromatography (SEC) was used to evaluate the integration of the polymer in the liposomes. Chromatography methods, including SEC and ion exchange chromatography, allow the removal of free polymer chains from liposomes preparations. In SEC, liposomes can be separated from solutes with lower molecular weight by carefully choosing the gel. The Sepharose® CL-4B was evaluated. On a 1×20 cm column, both elution peaks overlapped (i.e., liposome and free polymer). We then explored whether varying the length and inner diameter of the column could result in better separation.

Figure 1A:
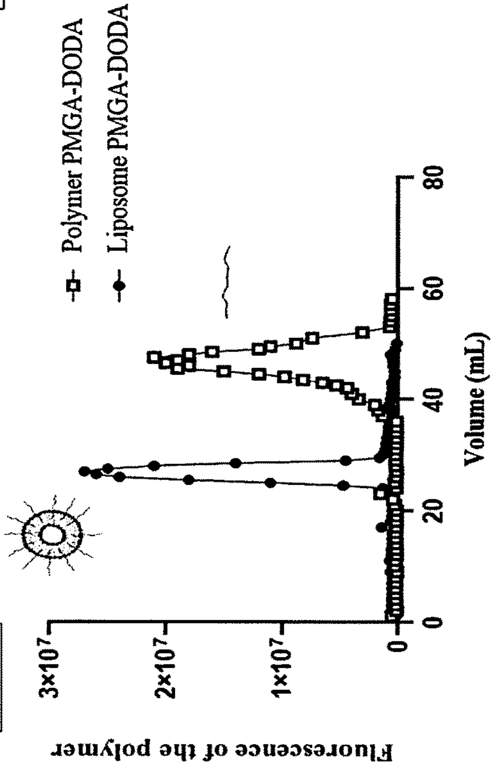

FIG. 1 shows that cross-linked acrylamide gels (Sepharose CL-4B, 2x50 cm) allows the separation of liposomes from free polymer by SEC. When CTA-PMGA-DODA or PMGA-DODA polymers are loaded in solution (i.e., in the absence of liposomes), they are retained in the gel and exit the column at elution volumes between 30 and 60 mL. When the polymer is prepared in a liposomal formulation, it is incorporated to a structure with a larger hydrodynamic radius (i.e., the liposomes). This alters its interactions with the column as it becomes too large to enter the pores of the gel, and the polymer exits at elution volumes of 22-30 mL (i.e., with the liposomes). The elution volume of the liposomes was confirmed in a parallel experiment in which liposomes (Liposomes HSPC or control liposomes) were revealed by post-column addition of Nile Red. This data confirms that the polymer is properly anchored to the liposome. Comparing the degree of incorporation into liposomes for CTA-PMGA-DODA and PMGA-DODA (with and without the dodecyl Z group), we observed no difference, suggesting that the removal of the C-12 alkyl chain does not prevent anchoring of the polymer to the vesicle (FIG. 1).

Figure 2:
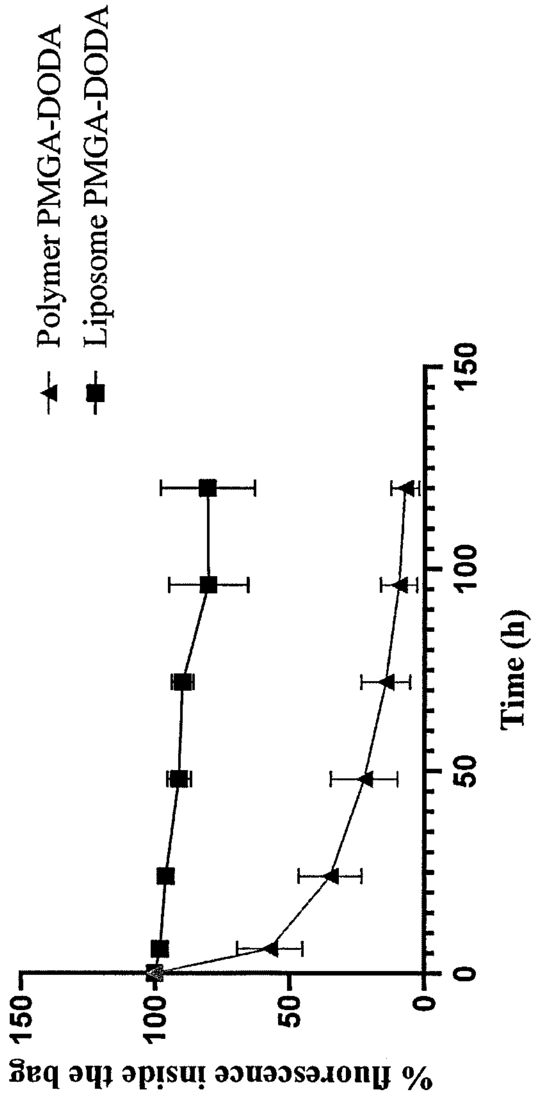
FIG. 2 represents that dialysis can be used to confirm the anchoring of the polymer into the bilayer. Measures of the fluorescence inside the dialysis bag at different time point for the polymer and the liposome formulation show that the polymer on the liposome remains on the surface of the vesicle. The value represented a mean±standard deviation (n=3).

Since polymeric micelles can be a drug delivery platform on their own, defined by their thermodynamic stability, these experiments emphasize that the system we are using is liposomes and not micellar structures. Indeed, it is known that amphiphilic structures can self-assemble on their own to created micellar structures. We characterized the critical micellar concentration (CMC) of the polymers to evaluate their ability to self-assemble into polymolecular structures. It is generally accepted that increasing the percentage of hydrophobic block results in a decrease of the CMC, suggesting polymers require fewer molecules to form micelles as discussed in *Journal of Controlled Release* 2005, 109 (1), 169-188. As expected, the polymer with the dodecyl moiety (CTA-PMGA-DODA) appears to have a lower CMC than the polymer on which the Z group was hydrolyzed (PMGA-DODA) (Example 4ii). To further confirm that the results of the Sepharose® CL-4B SEC are truly representative of interactions with liposomes and not the formation of micelles but also to monitor the stability of the PMGA-DODA anchoring on the liposome, we performed dialysis using the fluorescent polymer. This technique relies on the diffusion of molecules through a semi-permeable membrane to separate solutes from larger colloids. This technique can be used for purification or to study the speed at which drug delivery system (DDS) release their encapsulated molecules as shown in *Chemical industry press.* 2015, 1*st edn.,* 175-177. In FIG. 2, we used a dialysis membrane with a molecular weight cut-off (MWCO) larger than the polymer chains (100 kDa). This allows the free polymer to diffuse out of the dialysis bag while retaining the liposomes that have a larger hydrodynamic radius. In the present case where the amphiphilic polymer possibly forms self-assembled architectures, a dynamic equilibrium exists between individual molecules and micellar structures. Here, we measured the fluorescence inside the dialysis bag over a period of 120 hours. The results showed that after only 6 hours, 43% of the free polymer from the micellar formulation is removed compared to 1% of the polymer into the liposome formulation. After 120 hours, <10% of the initial fluorescence remains in the bag of the micelle suspension, compared to >80% for the liposome (FIG. 2). This difference in the kinetic of diffusion confirms that most of the polymer remains anchored into the bilayer of the liposome for at least a period of 5 days.

Furthermore, we wanted to understand if the incorporation of the PMGA to liposomes can affect their stability in different conditions. To do that we used a water-soluble fluorescent dye (HPTS, trisodium 8-hydroxypyrene-1,3,6-trisulfonate) and encapsulated it with a proximity quencher (DPX, p-Xylene-Bis-Pyridinium Bromide) inside the aqueous cavity of the liposome. This system allows monitoring the disruption of the vesicles by a strong increase in fluorescence when the dye and the quencher are released in the surrounding environment. Liposomes were exposed to different osmotic pressures by varying the concentration of salt in the media (20-5000 mOSm/L).

Figure 3:
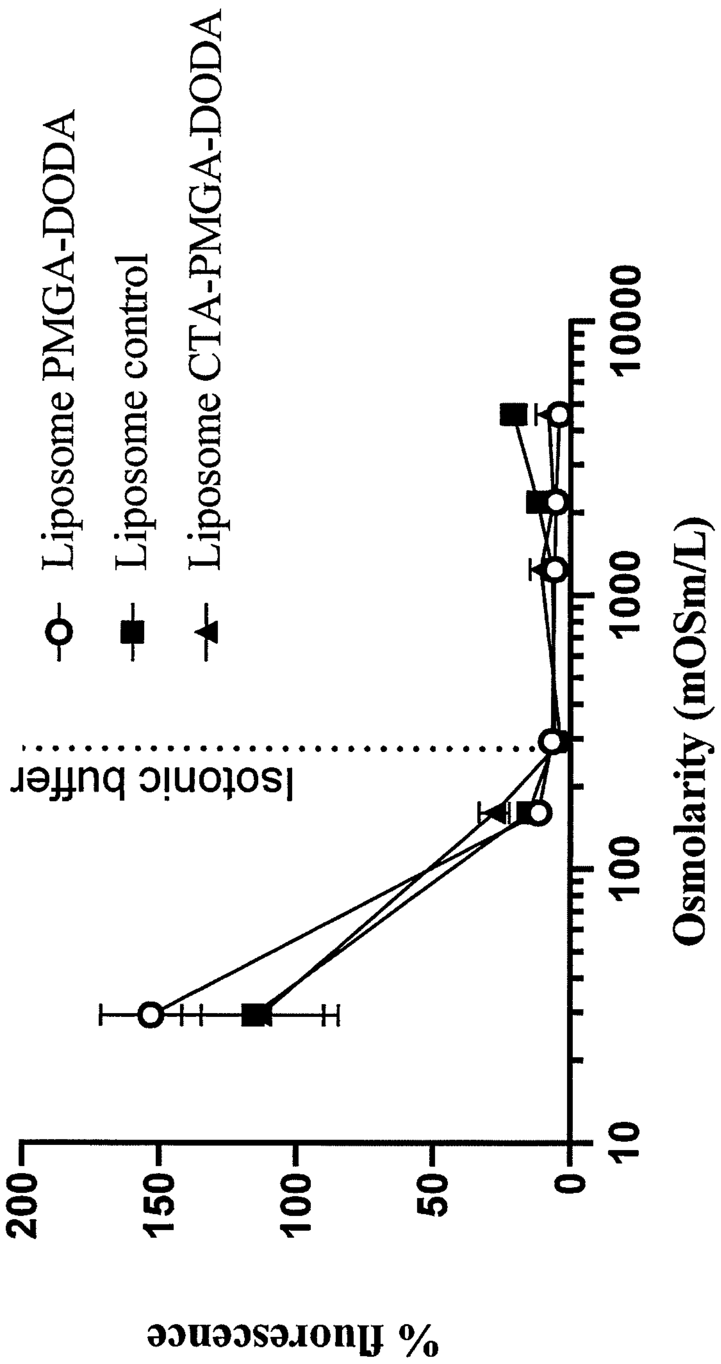
FIG. 3 represents the measure of the osmotic shock and shows that incorporation of the polymer to liposomes does not alter their stability. Release of the fluorescence was used to show the stability of the carrier under drastic condition (λex/em=450/512 nm). Liposome containing 10 mM HEPES, 35 mM HPTS and 50 mM DPX were used.

Osmotic stress imposed by salt gradients can result in the disruption of the phospholipid membranes of liposomes. Liposomes swell more rapidly under hypertonic conditions, compared to isotonic environments as reported in *Biochimica et Biophysica Acta* (*BBA*)—*Biomembranes* 1991, 1069 (1), 5-13. Interestingly, the release of the dye is much more important when put into a hypotonic medium. In fact, all the content inside the liposome is released drastically in hypotonic solutions (FIG. 3). This release of the liposome content is the result of the diffusion of water through the phospholipid bilayer. However, very little difference is observed in the osmotic stability of liposomes prepared with and without PMGA polymers. This suggests that the incorporation of the polymer inside the vesicle membrane does not drastically affect the stability of the liposomes in these conditions.

Internalization of Different Cells Line

We evaluated the ability of liposomes prepared with PGMA to be internalized by different cell lines in vitro, using flow cytometry. Cellular internalization is critical for most drug delivery systems to deliver their drug content to cells. In this experiment, the liposomes were fluorescently labeled by the encapsulation of DiD' (1,1'-Dioctadecyl-3,3,3',3'-Tetramethylindodicarbocyanine, 4-Chlorobenzenesulfonate Salt) (λex/em: 655/675). The list of cells tested includes RAW 264.7 mouse macrophage-like lymphoma, primary dendritic cells derived from mouse, A20 mouse B cell lymphoma, U87-MG human glioblastoma cells and A549 human lung adenocarcinoma cell lines. FIG. 4 shows that compared to liposomes prepared without PMGA (control liposome), the cellular uptake of PMGA-DODA containing liposomes is much higher. To ensure that these differences were not ascribed to physicochemical properties such as size or charge, liposomes with and without PMGA were prepared with the same diameter and using the same phospholipids (HSPC and cholesterol).

Figures 4A, 4B, 4C, 4D:
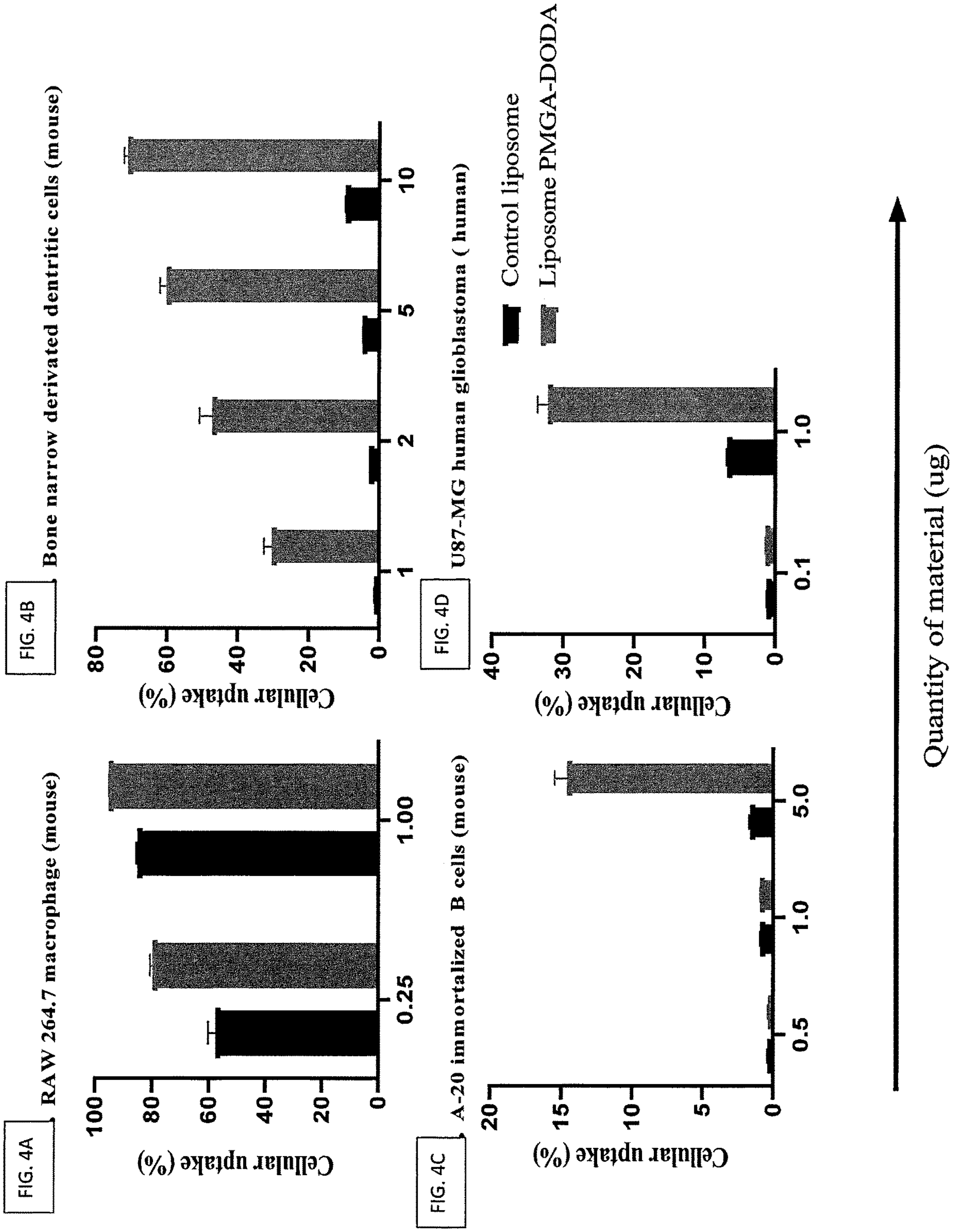
FIGS. 4A, 4B, 4C and 4D show that the PMGA increase the uptake in different cell line. Flow cytometry analysis with DID' (n=2).
Figure 5:
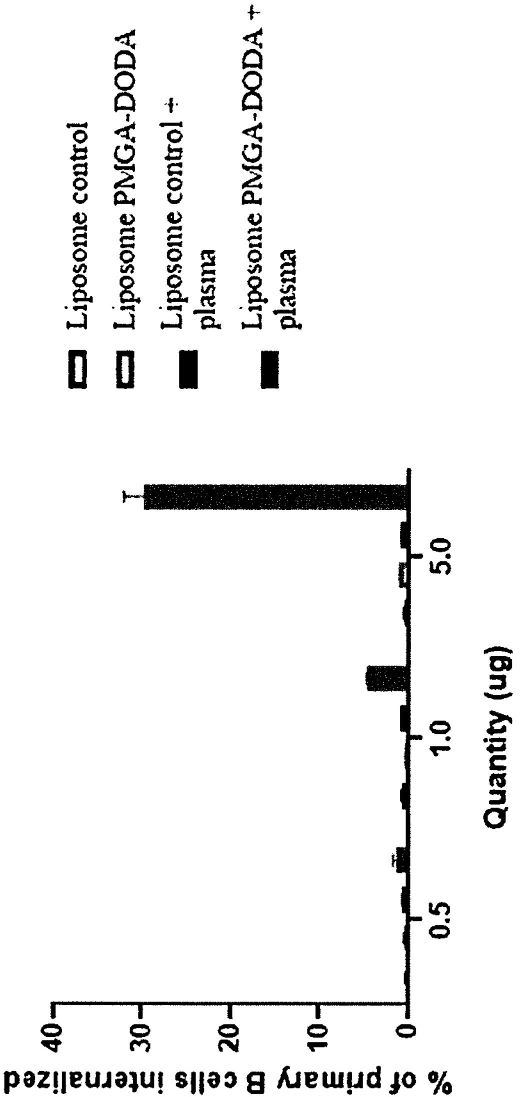
FIG. 5 shows that the increase in internalization by RAW 264.7 was preserved even in the presence of plasma when comparing the control liposome and the PMGA-DODA liposome.

Macrophages are specialized phagocytic cells found in every tissue of the body. Here we used RAW 264.7 cells that are monocyte/macrophage-like murine cancer cells generated through exposition to the Abelson murine leukemia virus. Due to their phagocytic properties, the cellular uptake of both control (liposome HSPC) and PMGA-liposomes is higher in this cell line (FIG. 4A). Above quantities of 1 μg, no differences could be perceived between formulations. Importantly, this increase in internalization was preserved even in the presence of plasma (FIG. 5), confirming that the deposition of proteins on the surface of liposomes (possibly resulting in the masking of epitopes) does not prevent the PGMA-mediated uptake.

Figure 6:
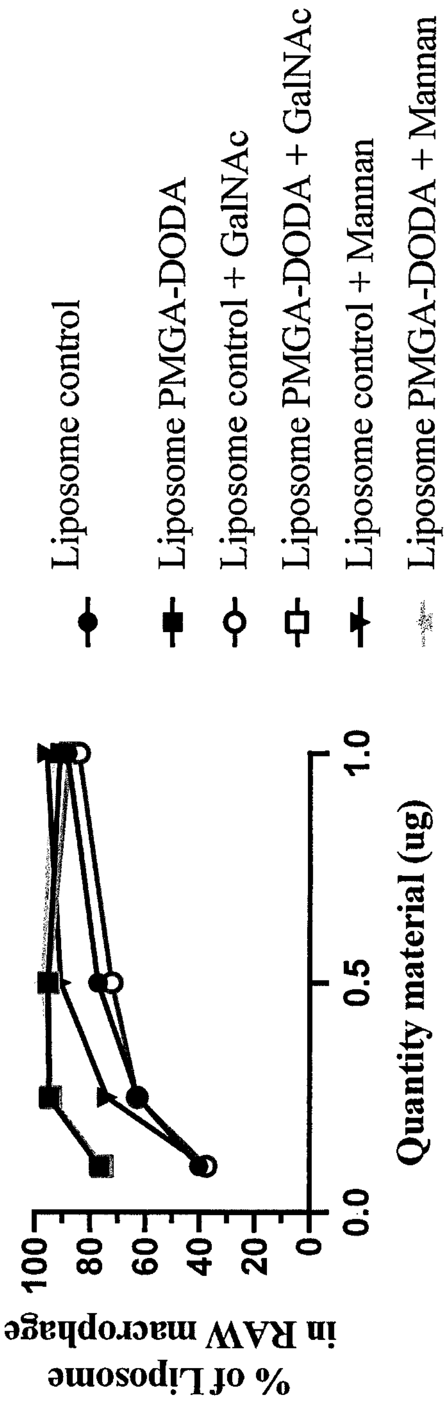
FIG. 6 represents the uptake of liposomes in RAW 264.7 macrophages. Competition with extreme concentration of Mannan or N-Acetylgalactosamine (GalNAc) to see if the uptake decreases. Flow cytometry analysis with DID' laser 640 (660/20 filter, n=2).

Murine primary dendritic cells were obtained by differentiation of mesenchymal stem cells, cellular uptake was performed 8 days after harvesting. In this cell line, the cellular uptake of PMGA-DODA containing liposomes is >20-fold higher than the control formulation (FIG. 4B). Supporting that PMGA-DODA significantly increases interactions with these cells, at all concentrations tested. Although the mechanism is still unclear, it is known that uptake in dendritic cells can be enhanced by bounding to the mannose receptors as reported in *Vaccine* 2003, 21 (9-10), 883-90. In RAW 264.7 cells, incubation of PMGA-DODA containing liposomes with competing mannan (a linear polysaccharide of mannose) did not decrease cellular internalisation, suggesting the mannose receptor might not necessarily be involved in cellular uptake (FIG. 6).

Figure 7:
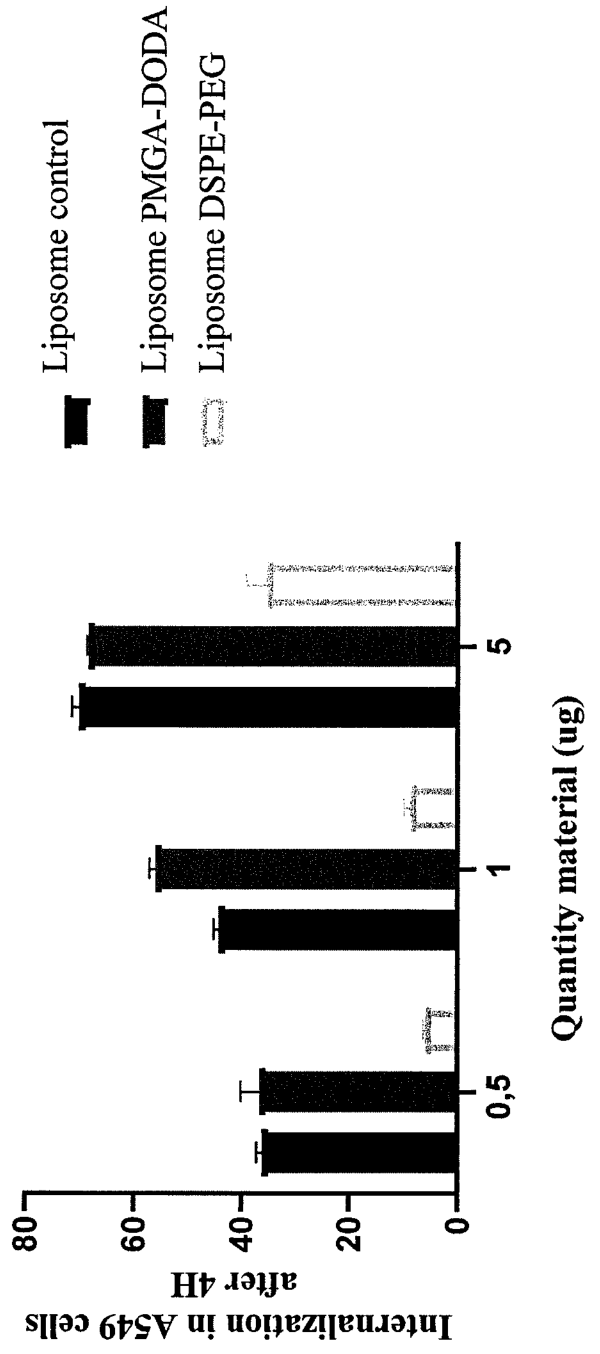
FIG. 7 shows the uptake in A549 lungs cells is not increased by coating with PMGA-DODA compared to the control liposome HSPC. Measure of the fluorescence of DID' by flow cytometry after incubation for 4 hours with the A549 cells line (n=3). Liposome DSPE-PEG is also used as a control (DSPE-PEG=1,2-distearoyl-sn-glycerol-3-phosphoethanolamine-N-[amino(polyethylene glycol)-2000]).

We also investigated the uptake of PMGA-DODA liposomes in cancerous B cells (A-20), as a model for another type of immune cells. Although this cell line has decreased internalization capacities, compared to primary B cells obtained from the spleen of mice (data not shown), the difference in cellular internalization between liposomes with PMGA-DODA and their control is mostly visible at high concentrations (FIG. 4C). Finally, experiments in U87-MG glioblastoma cell lines also confirmed that PMGA-decorated liposomes could be internalized more efficiently, again at higher concentrations (FIG. 4D). In all abovementioned experiments, the cells were incubated with the liposomes for a brief period of 2 hours. When cells were incubated longer, the differences between the PMGA-DODA liposomes and the control liposome decreased, mostly because all cells became fluorescent. In A549 cell lines, incubated for 4 hours with the liposomes, differences in internalization could only be observed at one concentration (FIG. 7). It therefore appears that PMGA-DODA could increase the rate of cellular internalization, which could have potential to deliver therapeutic modalities to certain cell types only exposed transiently to liposomes.

Animal Study, Profile of Pharmacokinetic and Biodistribution

Figure 8B:
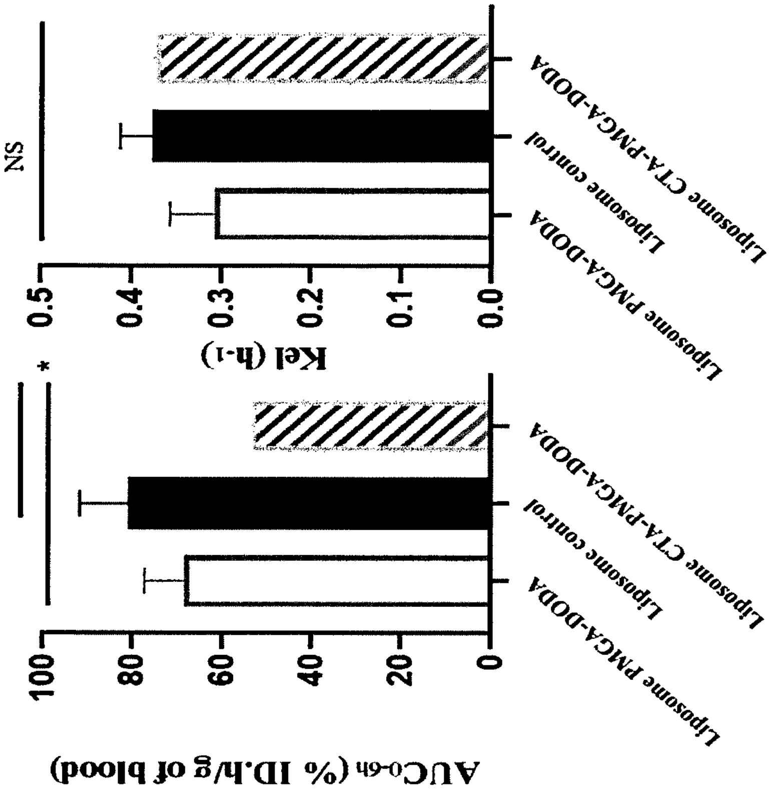
FIGS. 8A and 8B show that the CTA-PMGA-DODA polymer does not increase the circulation time of the liposome. Plasma clearance of the liposome with the polymer compared to liposome without any stabilizer on the surface after i.v. injection. Mice were intravenously injected with radiolabelled formulation ($^{14}C$). The blood was collected at different time point over 6 hours. The value represented a mean±SD (n=5-6).
Figure 8A:
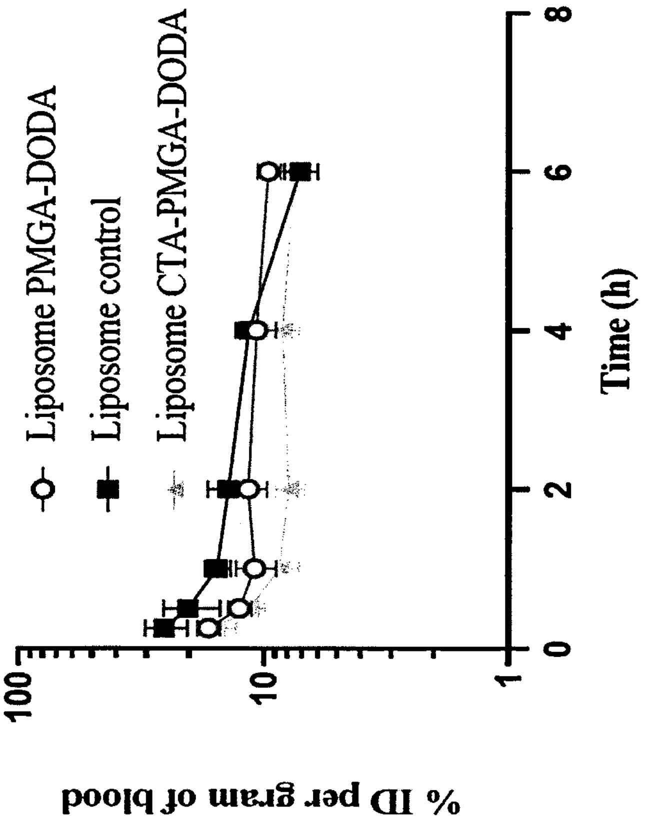
Figure 9:
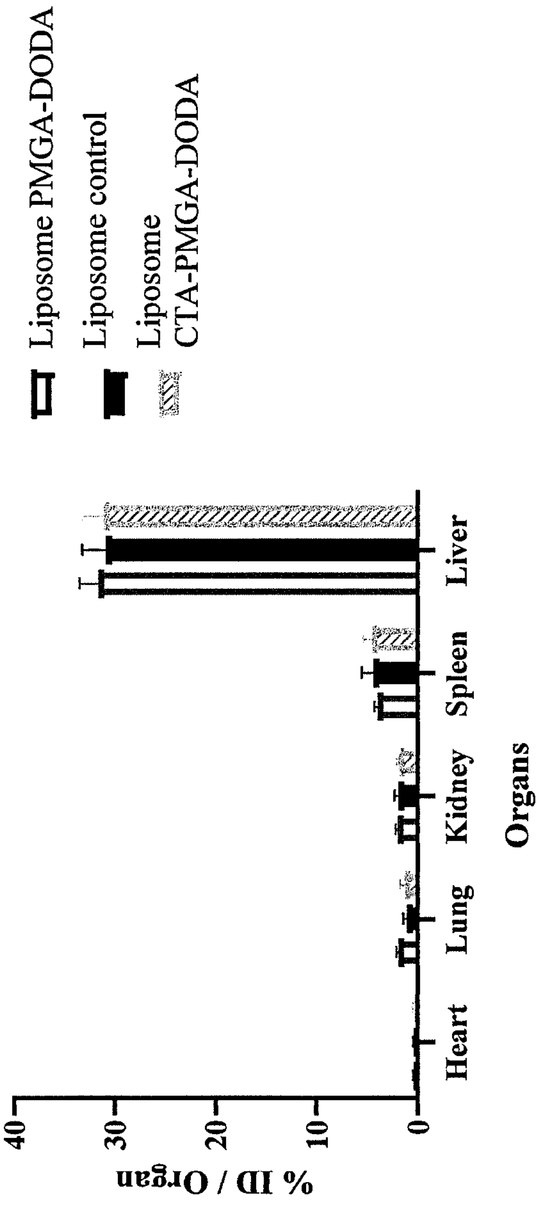
FIG. 9 represents the biodistribution of all the liposome formulation administered intravenously in mice. Data represent mean±SD (n=5-6).

The impact of CTA-PGMA-DODA and PMGA-DODA on the circulation profile of radiolabeled [$^{14}$C]-liposomes was studied in healthy Balb/c mice. In this study, the concentrations of radiolabeled liposomes in the blood were monitored for 6 hours after intravenous injection. The results of the experiment are presented in FIG. 8. Summary of the physicochemical characteristics of the different systems studied are presented in Table 4 (Example 6), while the pharmacokinetic (PK) parameters are presented in Table 5 (Example 6). The PK data suggests that CTA-PMGA-DODA and PMGA-DODA (i.e. with or without dodecyl chain) do not seem to prolong the circulation time of liposomes, since all circulation profiles are comparable. The blood exposure, as measured by the area under the blood concentration vs. time curve (AUC), appears to be slightly lower for the formulations prepared with PMGA compared to control liposomes without polymer. The $AUC_{0\text{-}6\ h}$ of the control liposomes is respectively 1.5 and 1.2-fold higher than those measured with the formulations prepared with CTA-PMGA-DODA and PMGA-DODA. This is possibly due to preferred interactions of PMGA-liposomes with various immune cells, as demonstrated in previous in vitro experiments. Of note, a small different exists between the PGMA formulations with and without the 12-carbon chain. After 1 hour from the injection and onwards, the blood concentrations of the formulation without the dodecyl end group (PMGA-DODA) are slightly higher than those observed for the polymer unmodified (CTA-PMGA-DODA). The amounts of formulation distributed to various organs (liver, spleen, lungs, heart, and kidneys) were similar for all three formulations (FIG. 9).

Figure 10A:
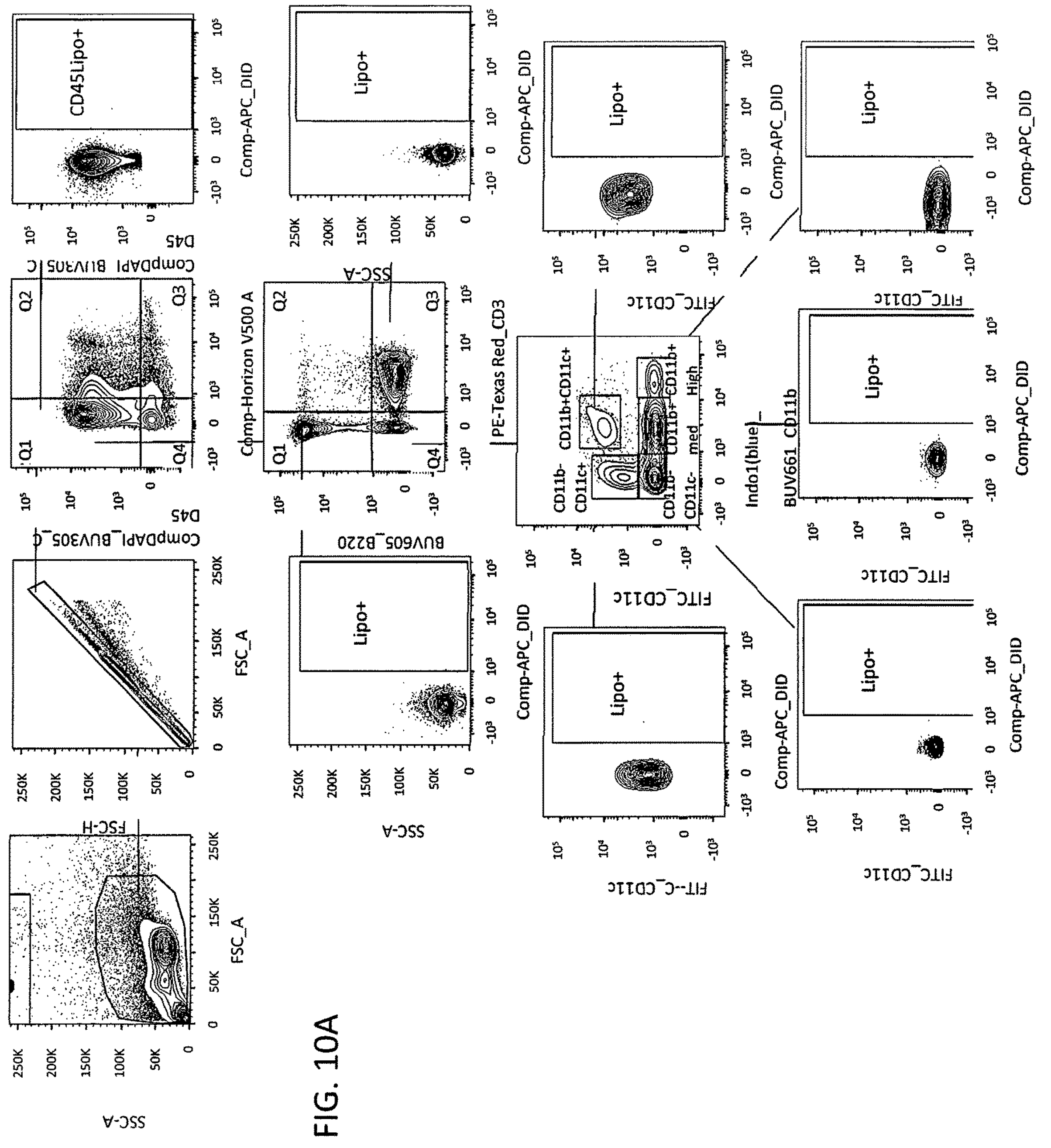
FIGS. 10A and 10B show the gating strategy for cellular distribution in spleen and lymph node.
Figure 10B:
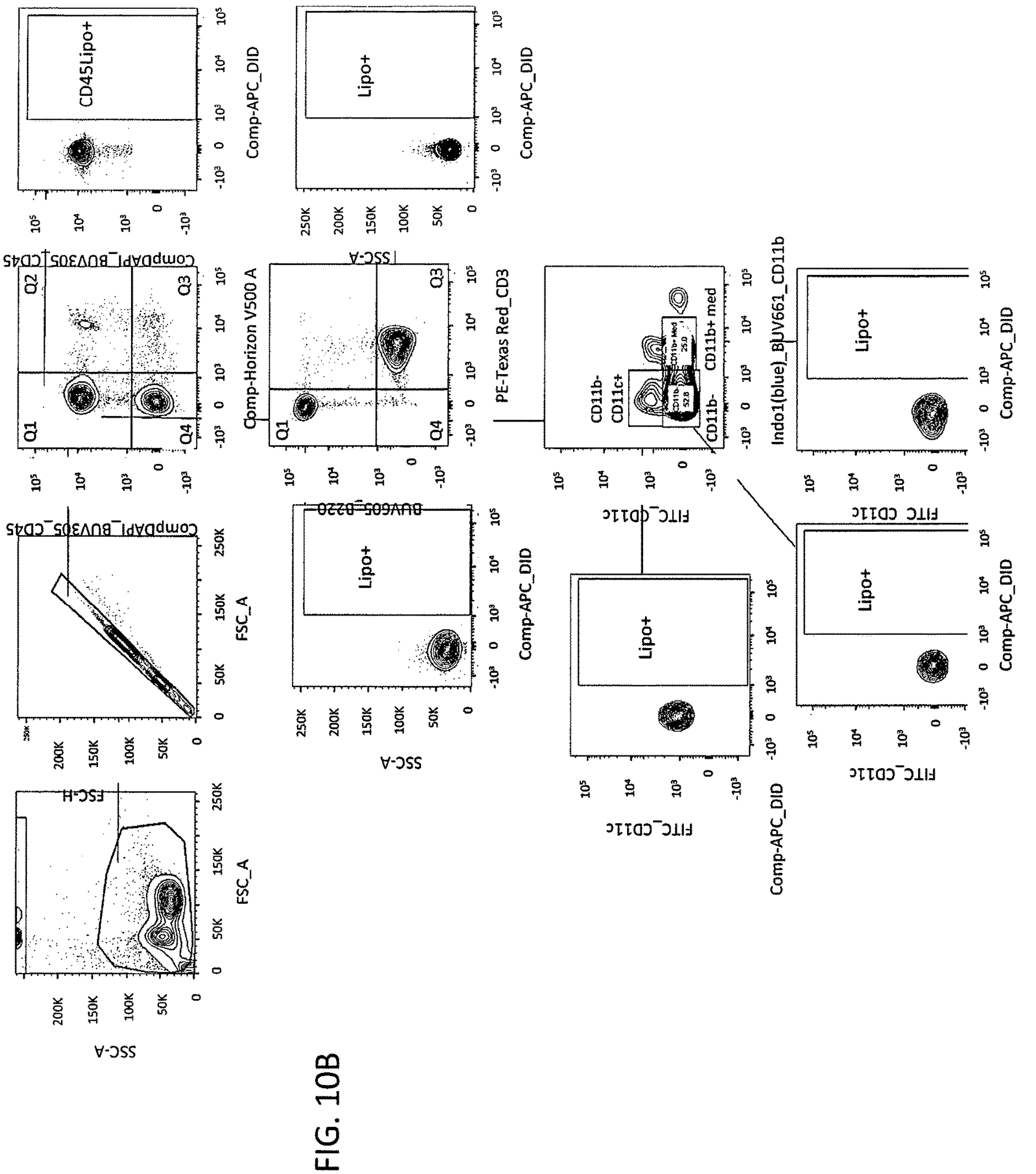
Figure 11:
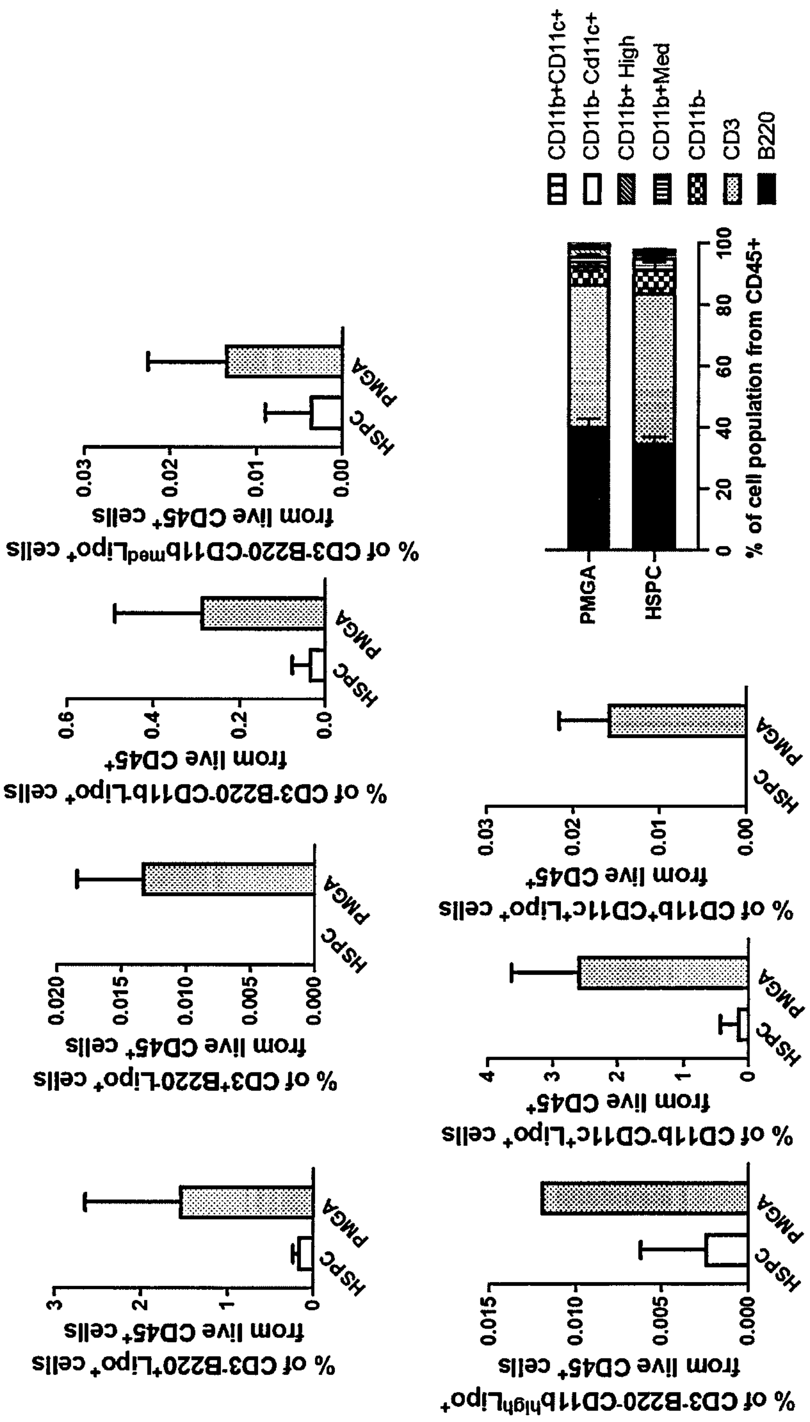
FIG. 11 represents the cellular distribution population in the spleen 24 hours after subcutaneous injection.
Figure 12:
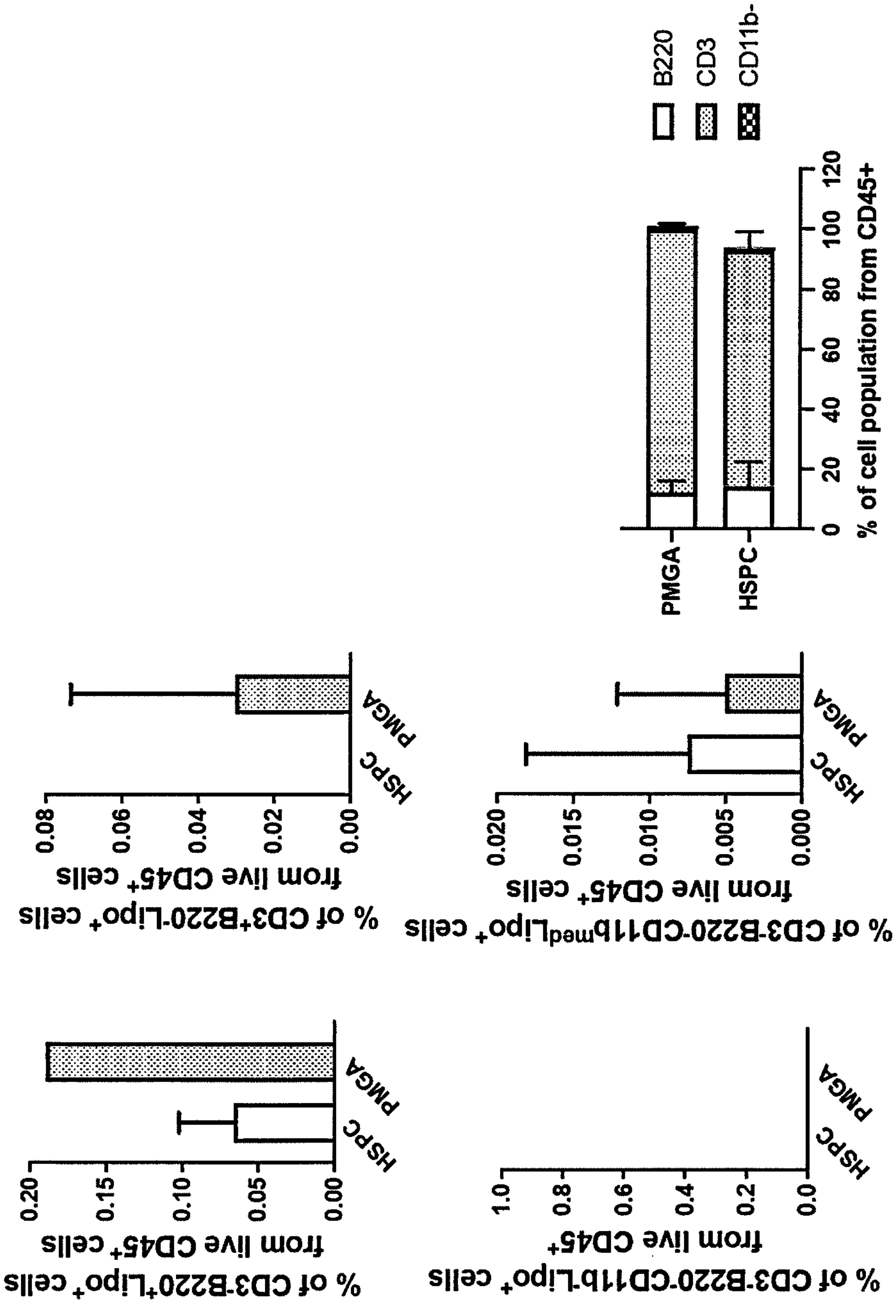
FIG. 12 represents the cellular distribution population in the lymph node 24 hours after subcutaneous injection.

To further understand the distribution of liposomes and to correlate it to in vitro results, we injected 2 mg/kg of DiD'-labeled liposomes with and without PMGA-DODA subcutaneously (hock injection) to healthy Balb/c mice. Twenty-four hours after injection, the spleen and lymph nodes were collected, and the cellular distribution was analyzed by FACS. Although the intensity of the fluorescence was barely above the limit of detection, the analysis shows an increase in uptake for CD45 positive cells when PMGA-DODA is present (FIGS. 10, 11 and 12). CD45 is usually present on all leukocytes, irrespectively of their origin (myeloid vs lymphoid). Other immunogenic markers allowed to narrow down which type of cells interacted with liposomes. Specifically, PMGA-DODA liposomes had higher distribution in B cells (CD3-B220+) and dendritic cells (CD11b-CD11c+), in the spleen. In the draining lymph node (popliteal lymph node ipsilateral to the injection), increased uptake in B cells (CD3-B220+) is observed with PMGA-DODA liposomes compared to control liposomes. These observations suggest that the preferential interactions of PMGA-DODA coated liposomes with immune cells are also perceptible in vivo. Indeed, in *Nature Biotechnology* 2007, 25 (10), 1159-1164, the authors reported that hydroxyl polymers coated on the surface of nanoparticles activate more the C3 fragment of the complement cascade, resulting in a higher uptake by specific cells. This goes in accordance with the fact that phagocytosis of nanoparticles can be engage by opsonic receptors following conformational changes as discussed in *Acta Pharmaceutica Sinica B* 2021, 11, 852-870.

Transfection of mRNA mRNA-based therapeutics hold a great future for new drug candidates. Hence, we tested whether PMGA could be used to prepare mRNA containing LNP. Using the ionizable lipid SM-102 and mRNA encoding for the green fluorescent protein (EGFP), we prepared LNPs. The composition of the LNP comprises: SM-102 as an ionizable cationic lipid, hydrogenated soybean phosphatidylcholine (HSPC) as helper, cholesterol for fluidity and either DMG-PEG or PMGA-DODA as steric and size self-assembled stabilizer (molar ratios respectively of 50:10:38.5:1.5 mol %). LNP with DMG-PEG were formulated as a control. Physicochemical analysis of the formulations showed that replacement of DMG-PEG with PMGA-DODA did not significantly impact the size of the LNPs or their efficiency of mRNA encapsulation (Table 6, Example 7). This confirms that PMGA-DODA can be used to prepare mRNA-containing LNPs comparable to the state-of-the-art.

Figure 13:
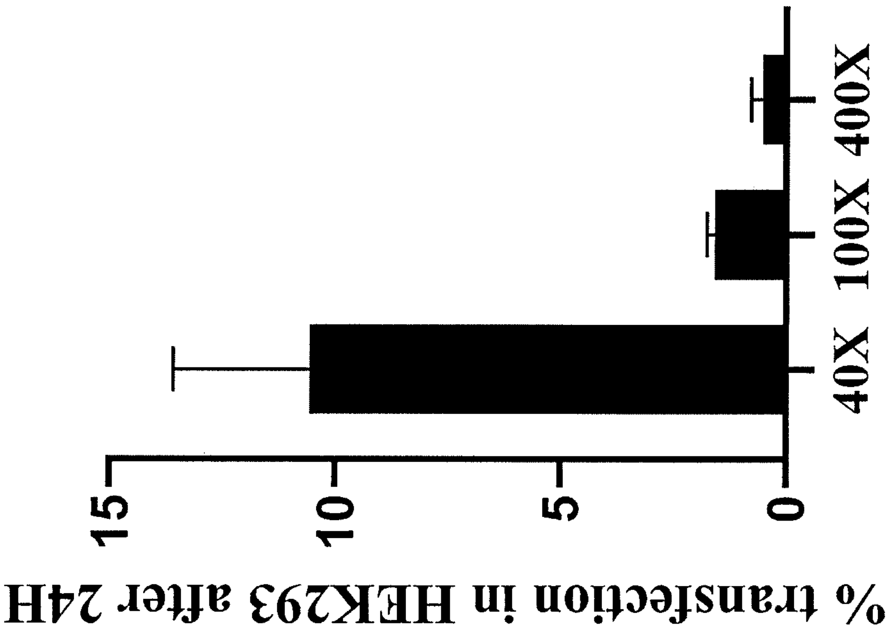
FIG. 13 shows that it is possible to do transfection with PMGA-DODA. Cleancap® EGFP mRNA was used to evaluate the transfection in HEK293 cells by cytometry with 488 laser (525/25 filter, n=3).

As a proof of concept, we tested the ability of PMGA-DODA LNPs to transfect HEK293 cells with EGFP. This cell line was chosen for its documented ease of transfection. FIG. 13 shows that PMGA-DODA decorated LNPs are able to transfect HEK293 cells. It is expected that further modification of the PMGA content or further adjustment of formulation parameters could enhance the transfection efficiency. These results show that PMGA-coated LNPs are credible candidates for gene delivery.

Cytotoxicity

Figure 14:
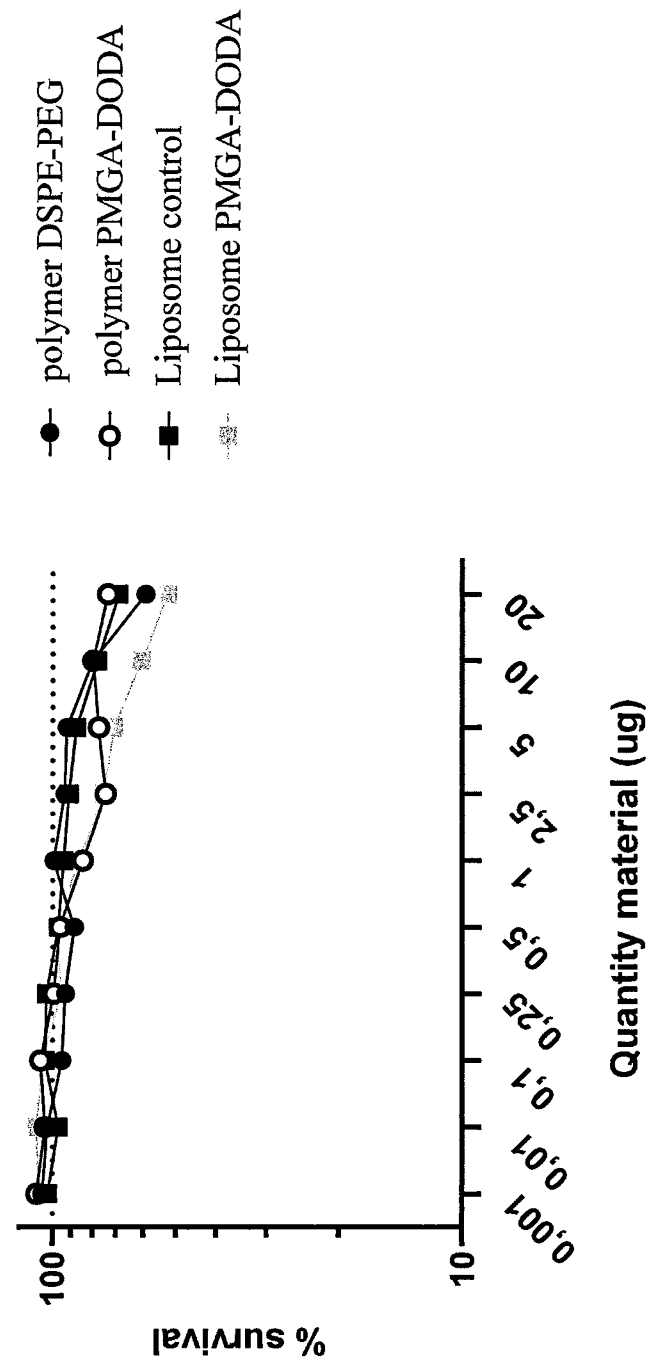
FIG. 14 shows that in vitro cytotoxicity of the PMGA-DODA is comparable to that of other amphiphilic polymer commonly used. It represents a MTT assay in RAW 264.7 used to study cell viability. Measure of the absorbance of formazan crystal (λ=570 nm).

We evaluated the cytotoxicity of PMGA-DODA in comparison to DSPE-PEG, a polymer-lipid already approved by the US-FDA as part of multiple drug products. Using the MTT assay (colorimetric assay for assessing cell metabolic activity), we compared the viability of a cell line exposed to increasing concentrations of the amphiphilic polymers, as well as liposomes containing PGMA or not. Reduction of the MTT reagent result in a disruption of the tetrazole ring and the formation of a violet-blue water insoluble molecule called formazan. The chromogenic nature of this redox chemical reaction provides a colorimetric based assay to measure the intracellular formation of this formazan when the cells are still alive. Cytotoxicity of liposomes and free polymer were studied on macrophages (RAW 264.7) incubated for 72 hours with concentration up to 20 μg/mL. The results showed that cell viability decreases with increase of material, as anticipated (FIG. 14). In this cell line, a decrease in macrophage survival is observed at concentrations of PMGA-DODA around 2.5 μg/mL, 10 times below the concentration at which DSPE-PEG starts to exhibit some toxicity (i.e., 25 μg/mL). This toxicity could be attributed to increased interactions between the polymer and this cell line.

Compositions, Formulations and Medical Uses

The polymers of the present description can be used to prepare lipid particles ("PMGA based lipid particles"), liposomes ("PMGA based liposomes"), polymeric nanoparticles ("PMGA-based polymeric nanoparticles") or lipid nanoparticles ("PMGA based nanoparticles") for use in the delivery of bioactive agents including nucleic acids (such as mRNA (messenger RNA), siRNA (small interfering RNA), shRNA (shorth harpin RNA), microRNA, gRNA (guide RNA)), small molecules, drugs, and proteins in vivo. PMGA based lipid particles include lipid nanoparticles, liposomes and lipid nanocapsules prepared with PMGA based polymers of the present description. PMGA based lipid particles and PMGA based polymer nanoparticles may include other lipids or polymers such as pegylated lipids or biodegradable polymers which are well known in the art.

In one aspect, the bioactive agent can be a therapeutic mRNA, which may code for a therapeutic protein. The mRNA may also be a mRNA encoding a vaccine antigen. In some instances, the mRNA may encode multiple proteins.

In one aspect, a lipid nanoparticle or liposome encapsulating an mRNA encoding a protein of interest (e.g., a therapeutic protein or a vaccine antigen) is provided in some aspects of the invention.

In certain embodiments, the lipid particle formulation comprises a cationic lipid, a non-cationic lipid (e.g., a phospholipid or fatty acid) and a structural lipid. In certain embodiments, the lipid nanoparticle formulation comprises a cationic lipid, a non-cationic lipid (e.g., phospholipid or fatty acid), a structural lipid, and an ionizable lipid.

In one aspect, lipid nanoparticle may be formulated using microfluidics technology such as NanoAssemblr Spark™. In one embodiment, the lipid nanoparticles may have a diameter from about 50 to 500 nm, from about 60 to about 500 nm, about 60 to about 400 nm, about 60 to about 300 nm, about 60 to about 200 nm, about 60 to about 100 nm, about 70 to about 100 nm, about 80 to about 100 nm, about 90 to about 120 nm and/or about 100 to about 200 nm.

In one aspect, liposomes are prepared using the thin film hydration method also known as the Bangham method. In one embodiment, the liposome may have a diameter may have a diameter from about 50 to 500 nm, from about 60 to about 500 nm, about 60 to about 400 nm, about 60 to about 300 nm, about 60 to about 200 nm, about 60 to about 100 nm, about 70 to about 100 nm, about 80 to about 100 nm, about 90 to about 120 nm and/or about 100 to about 200 nm.

In one embodiment the PMGA polymers can assemble in nanoparticles to form polymeric nanoparticles. Methods for preparing polymeric nanoparticles from polymers include emulsion-solvent evaporation, double emulsion and evaporation, emulsions-diffusion, solvent displacement, salting out and dialysis.

Compositions incorporating PMGA based lipid particles can include pharmaceutically acceptable carrier, diluent, or excipient. The expression "pharmaceutically acceptable carrier, diluent, or excipient" and equivalent expressions, refer to a non-toxic carrier, diluent, or excipient that does not destroy the pharmacological activity of the compound or lipid nanoparticle with which it is formulated.

Compositions described herein may be administered orally, parenterally, by inhalation spray, topically, rectally, nasally, buccally, or via an implanted reservoir. The term "parenteral" as used herein includes subcutaneous, intravenous, intramuscular, intraarticular, intrasynovial, intrasternal, intrathecal, intrahepatic, and intralesional injection or infusion techniques. Other modes of administration also include intradermal or transdermal administration.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The amount of compound that may be combined with carrier materials to produce a composition in a single dosage form will vary depending upon the patient to be treated and the particular mode of administration.

As used herein, the term "effective amount" means that amount of a compound that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in treatment, healing, prevention, or amelioration of a disease, disorder, or symptom thereof, or a decrease in the rate of advancement of a disease or disorder. The term also includes within its scope amounts effective to enhance normal physiological function.

As used herein, the terms "treatment", "treat", and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "vaccine" refers a therapeutic of preventive treatment of a disease or disorder. In some embodiments, a vaccine capable of eliciting an immune response in a subject or patient may be administered as a prophylaxis to prevent an infection by an infectious agent such as a virus. Vaccines include preparations that are capable of providing immunity against one or more conditions related to infectious diseases such as influenza, coronavirus (e.g., SARS COV-2 and variants), measles, human papillomavirus, rabies, meningitis, whooping cough, tetanus, plague, hepatitis, and tuberculosis and can include mRNAs encoding infectious disease derived antigens and/or epitopes. Vaccines also include preparations that direct an immune response against cancer cells and can include mRNAs encoding tumor cell derived antigen and/or epitopes. In some embodiments, a vaccine capable of eliciting an immune response can be administered intramuscularly via a composition including a PMGA based polymers as defined herein.

The term "patient" or "subject" as used herein refers to an animal such as a mammal. A subject may therefore refer to, for example, mice, rats, dogs, cats, horses, cows, pigs, guinea pigs, primates including humans and the like. Preferably the subject is a human.

It will be understood that the total daily dose of the compound will be decided by the attending physician within the scope of sound medical judgment. For instance, a specific dosage or treatment regimen for any particular patient will depend upon a variety of factors, including age, body weight, general health, sex, diet, time of administration, rate of excretion, drug combination, the judgment of the treating physician, and the severity of the symptoms associated with the disease or disorder.

EXAMPLES

The following non-limiting examples are illustrative embodiments and should not be construed as further limiting the scope of the present invention. These examples will be better understood with reference to the accompanying figures. The polymers used or described in the present may be prepared by conventional chemical synthesis such as those described in the Examples section below. Additionally, the various synthetic steps may be performed in an alternate sequence or order to give the desired compounds.

Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Example 1—Preparation of Starting Materials (i) Preparation of DODA-CTA

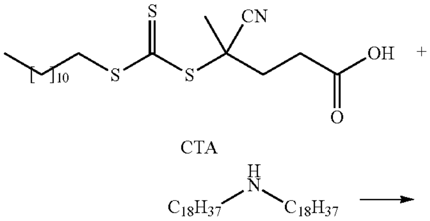

CTA

DODA

-continued

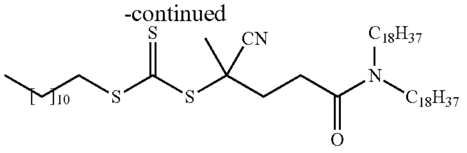

DODA-CTA

Figure 15:
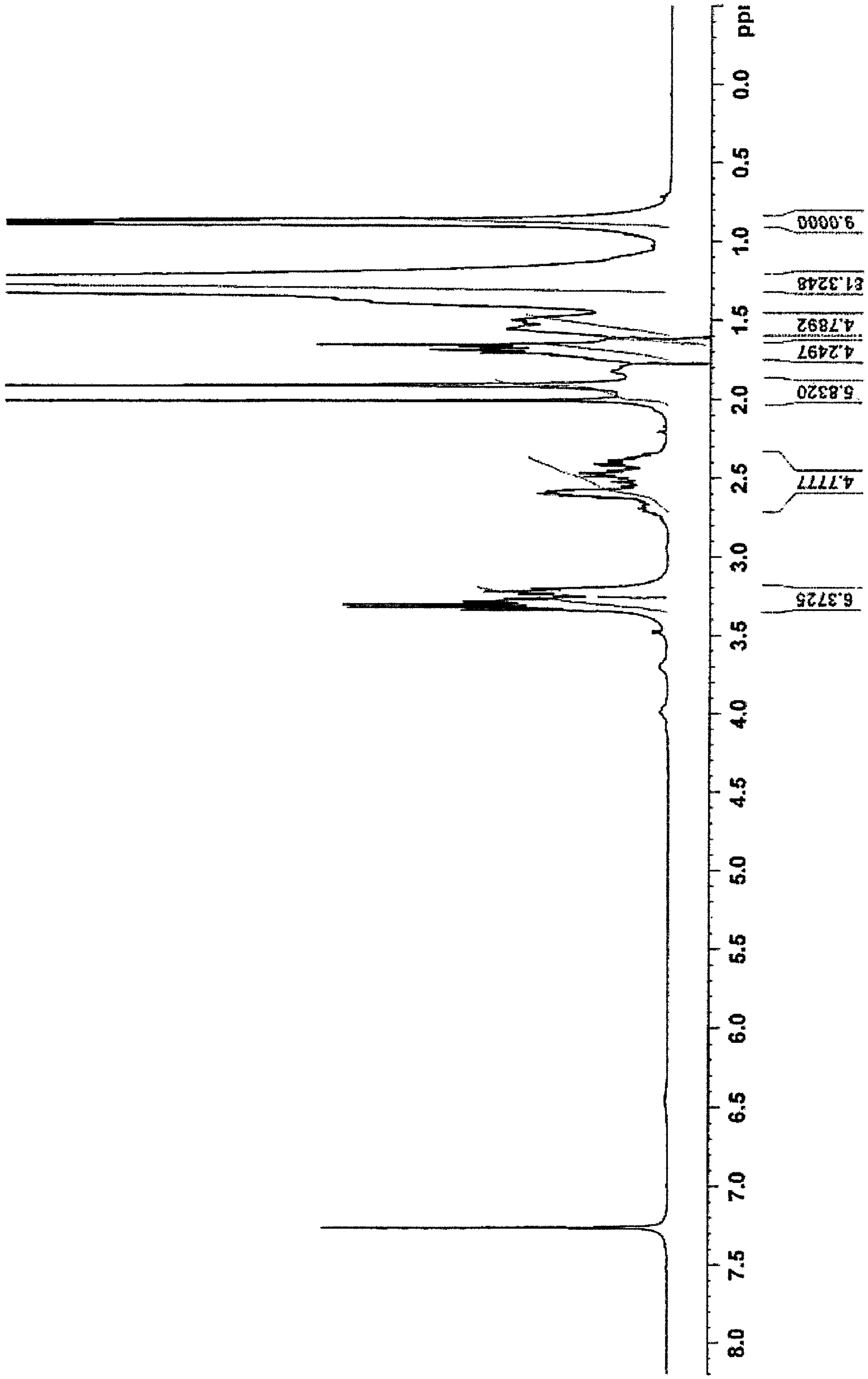
FIG. 15 shows the $^1$H NMR spectrum of the DODA-CTA.

The alkyled transfer agent was prepared according to the following procedure: 1.5895 g (3.33 mmol) of 4-cyano-[4 (dodedyl sulfanyl thiocarbonyl) sulfanyl] pentanoic acid (CTA), 2.5692 g (4.92 mmol, 1.25 eq) of dioctadecylamine (DODA), 1.0151 g (4.92 mmol, 1.25 eq) of dicyclohexylcarbodiimide (DCC), 686 μL (0.5 g, 3.93 mmol) of diisoproprylethylamine (DIPEA) in 40 mL of chloroform were reacted together overnight under an inert atmosphere. To confirm completion of the reaction, thin-layer chromatography was used with a mobile phase of 2:1 hexane/ethyl acetate (EtAc) and revealed with ninhydrin solution (200 mg of ninhydrin in 100 mL ethanol). At the end of the reaction, chloroform was evaporated to dryness under reduced pressure on a rotary evaporator, solubilised in a small quantity of a 2:1 v/v mixture of hexane and EtAc, and purified by silica gel chromatography. The product was identified by thin layer chromatography and all fractions containing DODA-CTA were pooled together. Evaporation of the solvent afforded an orange/brown viscous liquid. Finally, the product was solubilised in a small quantity of chloroform and precipitated in acetonitrile. The structure was confirmed (FIG. 15) by $^1$H NMR ($CDCl_3$, 400 MHz): δ 0.90 ppm (9H, t, J=6 Hz, —$CH_3$), 1.10-1.50 (78H, m, alkyl chain), 1.70 (3H, t, J=7 Hz, C(CN)—$CH_3$), 1.80-2.10 (6H, m, $CH_2$—$CH_2$—N—$CH_2$—$CH_2$—, —$CH_2$—$CH_2$—C—), 2.50 (2H, m, —$CH_2$C(═O)—), 3.50 (6H, m, —$CH_2$—N—$CH_2$—).

(ii) Preparation of Solketal Acrylate (SKA)

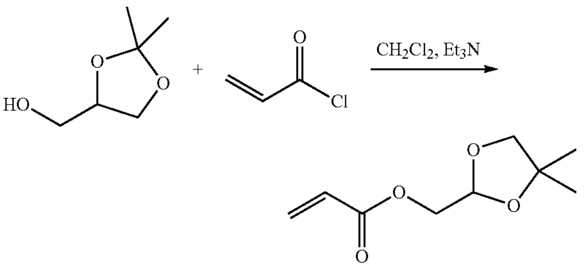

SKA

Figure 16:
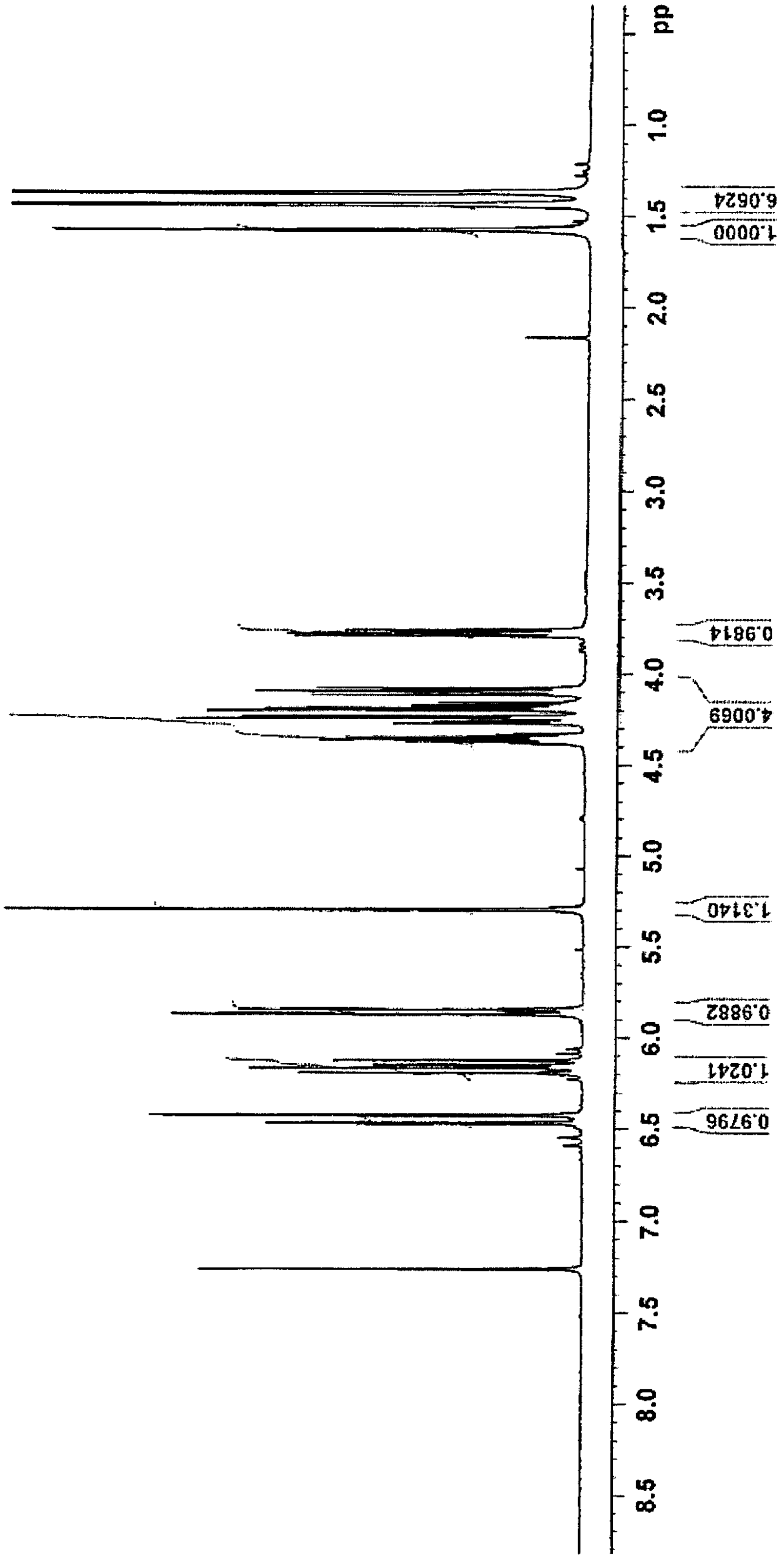
FIG. 16 shows the $^1$H NMR spectrum of the solketal acrylate (SKA).

The synthesis of SKA was achieved according to the following the procedure: at room temperature, triethylamine (40 mL, 0.29 mol) was added slowly to a mixture of solketal and acryloyl chloride (20 mL, 0.25 mol) in dichloromethane (200 mL). The round bottom flask was kept in an ice bath, during the addition of triethylamine. The reaction was left to stir for 6 hours at room temperature. The salt of triethylamine hydrochloride was filtered under vacuum and washed twice with 20 mL of dichloromethane. The filtrate was then washed thrice with a saturated aqueous solution of $NaHCO_3$ to remove all the triethylamine. The organic layer was dried over anhydrous $MgSO_4$ and the solvent was evaporated under reduced pressure to give an orange product (FIG. 16). $^1$H NMR ($CDCl_3$, 400 MHz): δ 1.04 ppm (3H, s, —$CH_3$), 1.30 (3H, s, —$CH_3$), 3.75 (1H, dd, J=2-7 Hz, —CHO—), 4.10-4.40 (4H, m, —$OCH_2$—), 5.85 (1H, dd, J=2-10 Hz $CH_2$═CH—), 6.15 (1H, dd, J=6-10 Hz, —CHC(═O)—), 6.40 (1H, dd, J=2-17 Hz, $CH_2$═CH—).

(iii) Preparation of Monomer Glycerol Acrylate

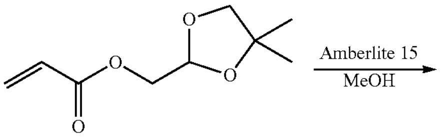

SKA

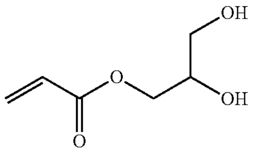

MGA

Figure 17:
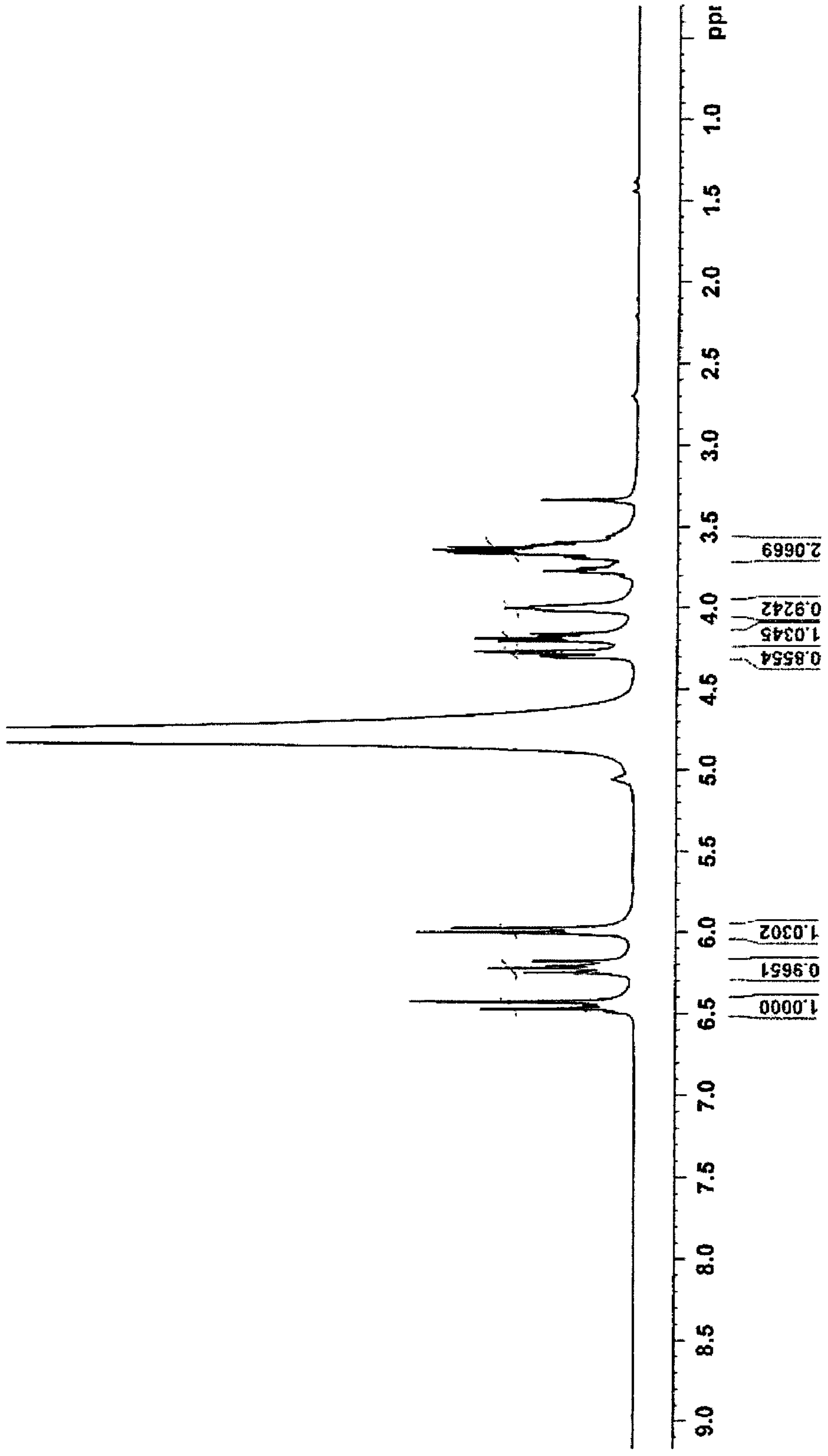
FIG. 17 shows the $^1$H NMR spectrum of the monoglycerol acrylate (MGA).

The deprotection of the acetal group of solketal acrylate was conducted according the following procedure: 1,589 g of Amberlyst 15® resin was hydrated by gentle stirring in 7 mL of methanol during 30 minutes. The methanol was removed by filtration and 80 mL of a methanol solution of solketal acrylate (7.8 g, 41.9 mmol) was added to the resin and stirred for 2 hours at room temperature. The reaction was filtered and washed with 30 mL of methanol and the solvent was removed by evaporation under reduced pressure to yield a brownish product. To remove impurities and unreacted material, the crude monoglycerol acrylate was dissolved in 10 mL of ultrapure water. The solution was extracted with 100 mL of chloroform and purified on a small alumina column (in a small glass pasteur pipette). $^1$H NMR ($D_2O$, 400 MHz): δ 3.65 (2H, t, J=5 Hz, —$CH_2$OH), 4.0 (1H, d, J=5 Hz, —CHOH), 4.15-4.4 (2H, dd, J=4-6 Hz, —$OCH_2$CH—), 6.0 (1H, d, J=10 Hz, $CH_2$═CH—), 6.25 (1H, dd, J=10 Hz, —CHC(═O)—), 6.5 (1H, d, J=17 Hz, $CH_2$═CH—). (FIG. 17)

Example 2—Preparation of Monoglycerol Acrylate Based-Polymers

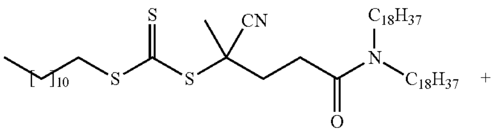

DODA-CTA

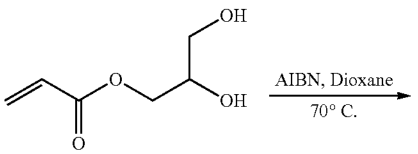

MGA

-continued

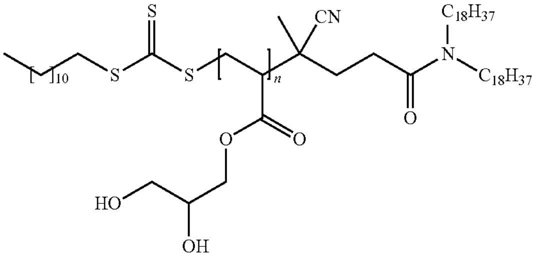

CTA-PMGA-DODA (i) Preparation of CTA-PMGA-DODA2k for n=10 (M=2, 000 g/mol)

Quantities are given for the synthesis of 1 g of polymer.

Reagents: 825 mg of monoglycerol acrylate (MGA), 312.2 mg of DODA-CTA and 5.6 mg of AlBN (molar ratio of MGA/DODA-CTA=1.2×10).

Solvents: 2.4 mL of methanol and 5.6 mL of dioxane.

Preparation method: the polymer CTA-PMGA-DODA2k was synthesized following the procedure described in (ii).

(ii) Preparation of CTA-PMGA-DODA6.5k for n=45 (M=6, 500 g/mol)

Figure 18:
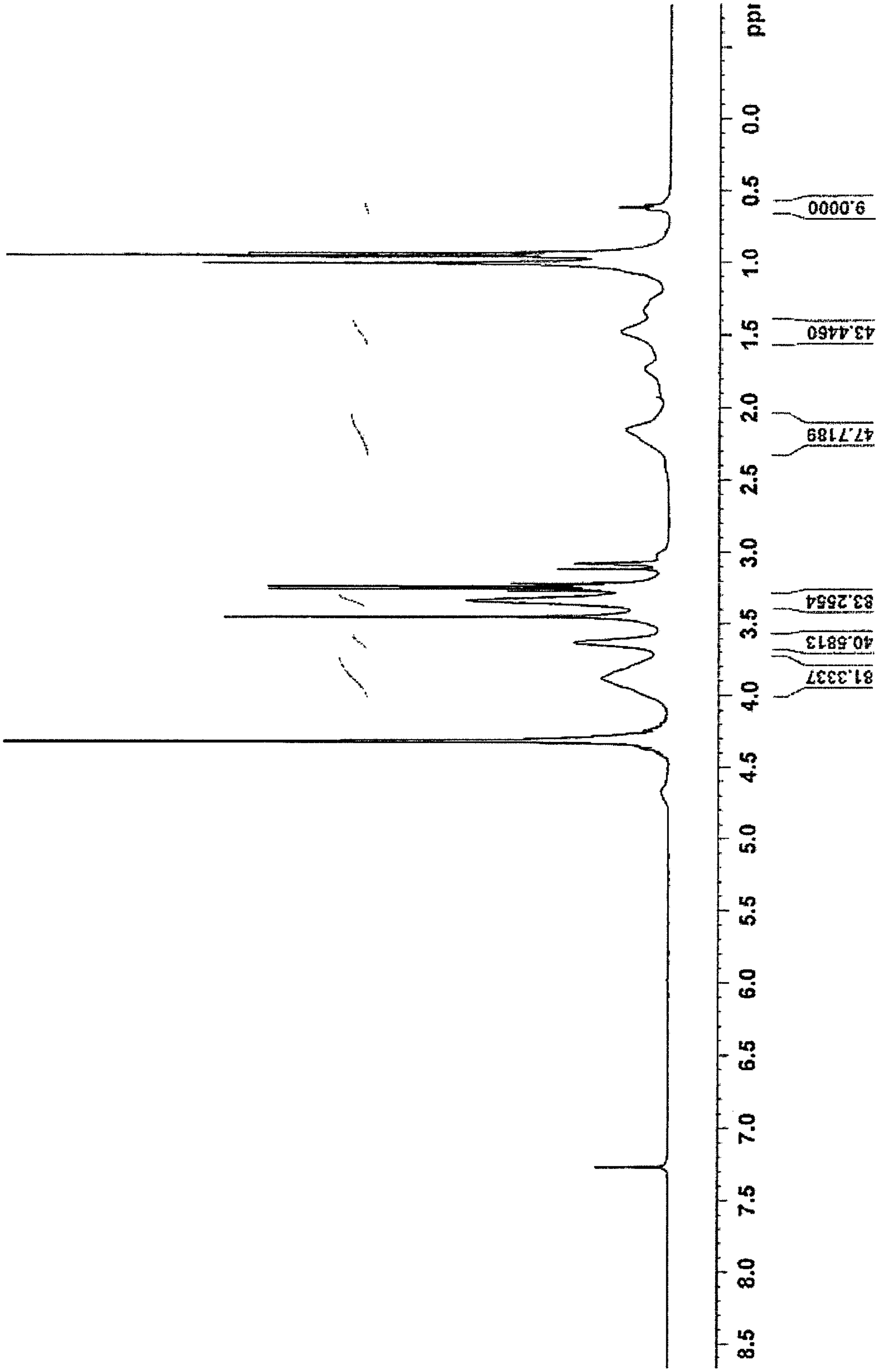
FIG. 18 shows the $^1$H NMR spectrum of the CTA-PMGA-DODA.
Figure 19:
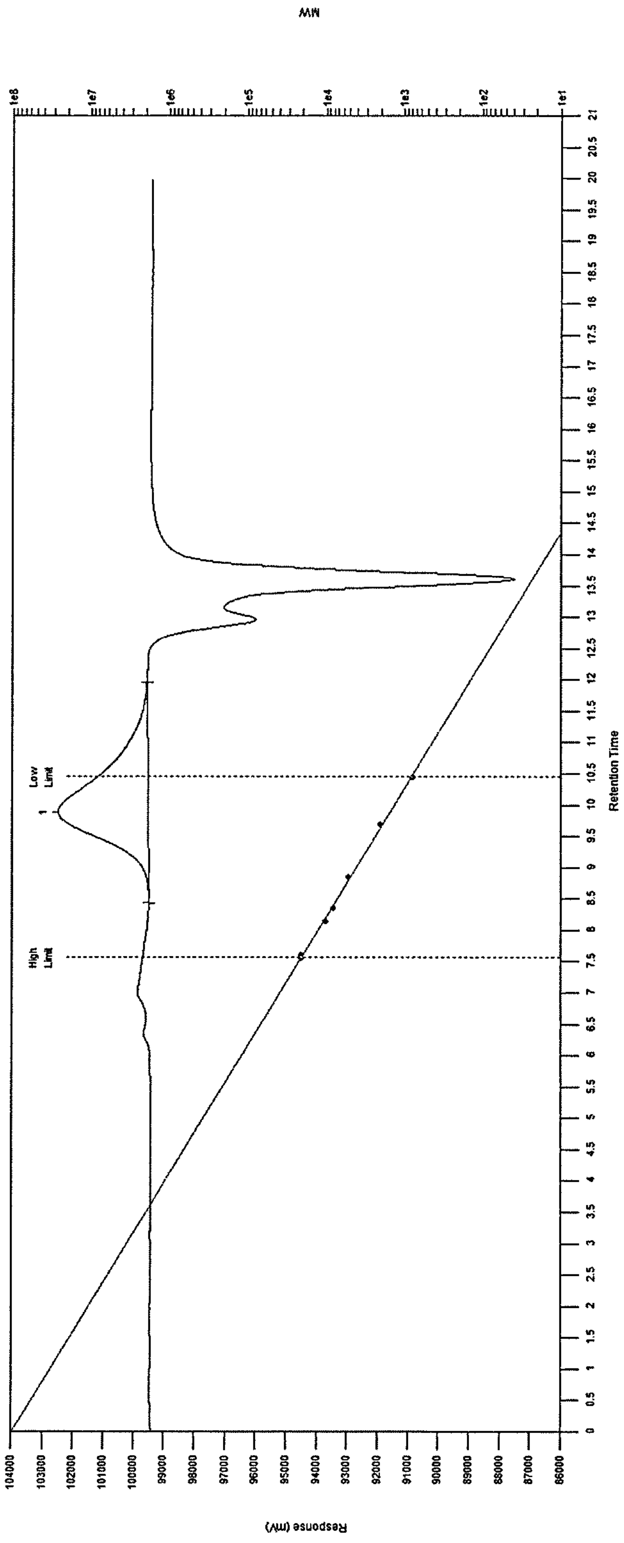
FIG. 19 shows the GPC chromatogram of the CTA-PMGA-DODA.

A typical procedure of polymerisation is the reversible addition-fragmentation chain transfer (RAFT) method. In a typical reaction to obtain a molecular weight of 6500 g/mol, 222 μL of a 10 mg/mL solution of azobisisobutyronitrile (AIBN) was added to MGA (1.053 g, 7.312 mmol) and DODA-CTA (122.6 mg, 0.135 mmol) in 9.1 mL of 1,4-dioxane and 3.1 mL of methanol. The solution was degassed by bubbling nitrogen for 15 minutes before initiating the reaction. The reaction was polymerised at 70° C. for 72 hours under stirring. The polymer was precipitated in a conical centrifuge tube (50 mL) of diethyl ether and freeze-dried. $^1$H NMR ($CDCl_3$/MeOD-d6, 400 MHz): δ 0.85 ppm (9H, t, $CH_3$), 1.20 (84H, m, alkyl chain), 1.50 (2H, s, —S[$CH_2$CH]—), 2.20-2.30 (1H, s, [$CH_2$CH]—), 3.30 (2H, s, —$CH_2$OH), 3.65 (1H, s, —CHOH), 3.80-4.0 (2H, s, —$OCH_2$CH—). (FIG. 18) In addition, the polydispersity index (Mw/Mn) was determined by gel permeation chromatography (GPC) with a PolySep-GFC-P 3000 column (300×7.8 mm, Phenomenex®) in 70% methanol and 30% ultrapure water (FIG. 19 and Table 1).

(iii) Preparation of CTA-PMGA-DODA10k for n=80 (M=10,000 g/mol)

Quantities are given for the synthesis of 1 g of polymer.

Reagents: 1116 mg of monoglycerol acrylate (MGA), 70.3 mg of DODA-CTA and 1.3 mg of AIBN (molar ratio of MGA/DODA-CTA=1.2×80).

Solvents: 4 mL of methanol and 8 mL of dioxane.

Preparation method: the polymer CTA-PMGA-DODA10k was synthesized following the procedure described in (ii).

(iv) Deprotection of CTA-PMGA-DODA to Give the DODA-Terminated Poly(Monoglycerol Acrylate) or PMGA-DODA

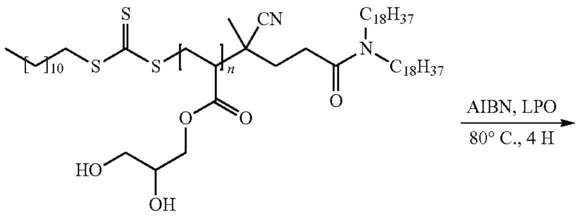

CTA-PMGA-DODA

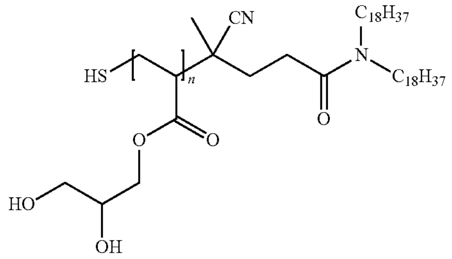

PMGA-DODA

The removal of thiocarbonylthio end groups by radical-addition-fragmentation was conducted as follows: [PMGA]:[AIBN]:[Lauroyl peroxide, LPO]=1:20:2. The reaction was reacted for 4 hours at 80° C. and precipitated in diethyl ether. The polydispersity index and change in molecular weight were determined by GPC (Table 1, Example 3).

Example 3—Preparation and Characterization of the Liposomes (i) Preparation of the Liposomes The liposomes were prepared by the hydration of lipid film followed by extrusion through polycarbonate membranes as follows: 40 mg/mL solutions of HSPC and cholesterol were prepared in 3:1 chloroform/methanol and stored at −20° C. until further use. The alkylated polymer solution was prepared at 20 mg/mL in methanol. In a round bottom flask, each of these solutions were added (693 μL for HSPC, 234 μL for cholesterol and 210 μL for PMGA-DODA or CTA-PMGA-DODA (both for polymer with n=45; M=6, 500 g/mol), which corresponds to $1.4\times10^{-6}$ mol) and the solvent was evaporated under reduced pressure for 1 hour at 50° C. The lipid film was hydrated with 600 μL of a HEPES saline buffer pH=7.4 (HEPES 20 mmol/L, 144 mmol/L NaCl) or 10 mM of HEPES buffer with 35 mM of 8-Hydroxypyrene-1,3,6-trisulfonic acid trisodium salt (HPTS) and 50 mM of p-xylene-bis-pyridinium bromide (DPX) pH=7.4 and sonicated for 1 hour. The HPTS/DPX buffer was used to prepare liposomes with quenched fluorescence for experiments studying the impact of osmotic shock. The solution was vortexed and hydrated at 4° C. for 24 hours. The suspension was then extruded while heating through 400-200-100-50 nm polycarbonate membranes (Whatman Nuclepore track-etched) using a LiposoFast manual extruder (Avestin). The size and polydispersity index (PDI) were confirmed by dynamic light scattering (DLS) using a Malvern Zetasizer Nano S (Malvern Instruments), at 22° C. with a 173°-backscatter angle. The phosphorous content was determined by a Bartlett phosphorous colorimetric assay, as described in detail elsewhere (*Food Chemistry* 2020, 126736 and *The Journal of biological chemistry* 1959, 234 (3), 466-468). Standard curve was prepared with potassium phosphate ($K_3PO_4$, dried overnight in an oven) in water at a range from 0 to 32 mM. Liposomes radiolabelled for the animal studies were prepared following the same procedure, but with smaller quantities: 23.1 μL of HSPC (40 mg/mL in chloroform), 7.8 μL of cholesterol (40 mg/mL in chloroform) and 20 μL of $^{14}$C-Cholesteryl oleate (0.1 μCi/μL) was added to the round bottom flask for the control liposome. Liposomes with CTA-PMGA-DODA also contained 14 μL (20 mg/mL in methanol) of the alkylated polymer. The same recipes were used for in vitro study but with a small quantity of 1,1'-Dioctadecyl-3,3,3',3'-tetramethylindodiocarbocyanine perchlorate (DID', 0.065 mg). For the liposome control 12 μL of DSPE-PEG (20 mg/mL in $CHCl_3$) was added to the rest of the formulation.

TABLE 1

Size and polydispersity index of all the formulations used for the different experiments.

| Formulation | Size (nm) | Polydispersity index (PDI) |
|---|---|---|
| Polymer CTA-PMGA-DODA$_{6.5k}$ | 110.5 | 0.218 |
| Polymer PMGA-DODA$_{6.5k}$ | 105.4 | 0.265 |
| Control liposome (HSPC/Cholesterol) | 104.6 | 0.054 |
| Liposome CTA-PMGA-DODA$_{6.5k}$ | 120.4 | 0.118 |
| Liposome PMGA-DODA$_{6.5k}$ | 123.8 | 0.097 |
| Polymer PMGA-DODA$_{6.5k}$ FITC-Cadaverine | 102.9 | 0.055 |
| Liposome PMGA-DODA$_{6.5k}$ FITC-Cadaverine | 113 | 0.082 |

(ii) Purification of the Liposomes

All the formulations of liposomes were purified by size exclusion chromatography. The void volume of the column (1×20 cm) was determined to use a control liposome with HSPC/Cholesterol (ca. 4.5 mL). Fraction containing liposomes was identified by adding 10 μL of a methanol solution of Nile red ($1\times10^{-5}$ M) as a hydrophobic dye since its fluorescence is well-known to be negligible in aqueous medium and instantly increase in hydrophobic environment found in membrane such as bilayer. Aliquot (100 μL) of each fraction was used to measure the fluorescence ((λex/em: 549/628 nm).

Example 4—Properties of the Liposomes (with Polymer with n=45; M=6,500 g/mol)

(i) Stability of the Polymer into the Bilayer—Synthesis of a Fluorescent Polymer as a Tracking Device

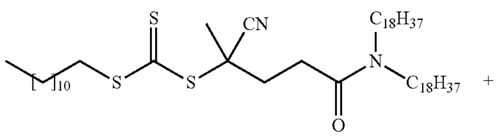

DODA-CTA

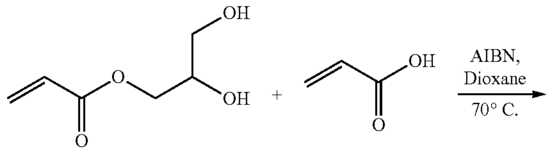

MGA

-continued

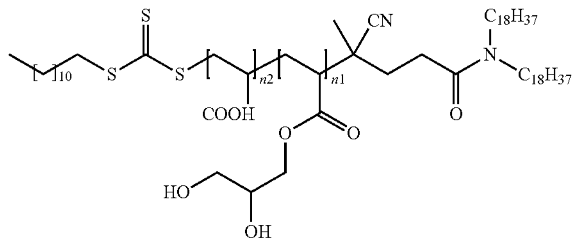

CTA-PMGA-DODA
1% acrylic acid

A fluorescent molecule was attached to the polymer as a label. 1% mol of acrylic acid was added to the RAFT reaction in order to get a carboxylic function where a terminal amine can be conjugated by peptide crosslinking.

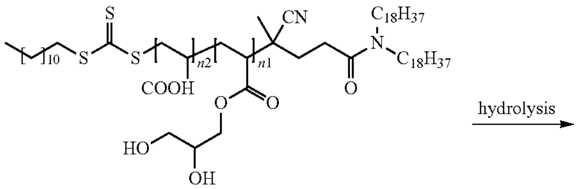

CTA-PMGA-DODA
1% acrylic acid

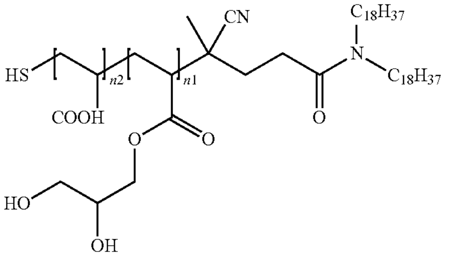

PMGA-DODA
1% acrylic acid

The procedure was conducted as follows: 100 mg of the alkylated polymer (PMGA-DODA with 1% of acrylic acid) was dissolved in 2 mL of carbonate buffer 0.1M pH=10.5 (sodium bicarbonate 12.5 mmol/L, sodium carbonate anhydrous 87.5 mmol/L). Then, 5 mg of 1-Ethyl-3-(3-dimethylaminopropryl)carbodiimide (EDC) and 1.725 mg of fluorescein cadaverine (2.40 μmol) was added to the mixture and left under stirring overnight. The polymer was dialyzed against water for 24 hours using a 3500 MWCO regenerated cellulose membrane (Spectra/Pore 3 dialysis membrane, RC trial kit), and the unreacted dye was further removed by purification on a Sephadex® G-75 column (20×1 cm).

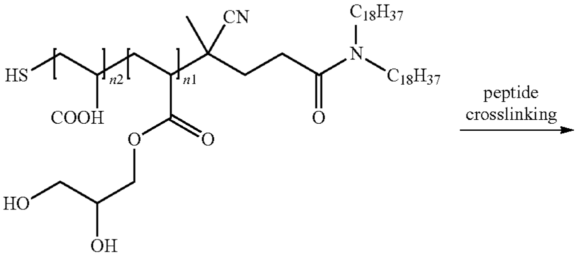

PMGA-DODA
1% acrylic acid

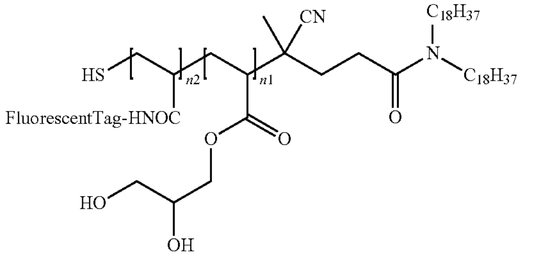

Fluorescent PMGA-DODA (ii) Critical Micellar Concentration (CMC)

Nile red can be used to measure the CMC of surfactants and polymolecular architectures by following the fluorescence of the dye: the critical micelle concentration coincides with a strong increase in the intensity of the fluorescence ($\lambda_{ex/em}$: 549/628 nm). Serial dilutions of polymers were made in the range of 2.5 to $7\times10^{-4}$ mg/mL. 200 μL of each sample were used with 10 μL of Nile Red solution in methanol ($1\times10^{-5}$ M). Fluorescence was read in a 96-well plate ($\lambda_{ex/em}$: 549/628 nm).

TABLE 2

Critical micelle concentration of the polymer DODA-PMGA compared to commercial products such has sodium dodecyl sulfate (SDS)

| Compound | DSPE-PEG | SDS | CTA-PMGA-$DODA_{6.5k}$ | PMGA-$DODA_{6.5k}$ |
|---|---|---|---|---|
| CMC (mg/mL) | 0.11 | 2 | 0.018 | 0.42 |

(iii) Polymer Incorporation into the Lipid Bilayer (for Polymer with n=45; M=6,500 g/mol)

Dialysis of the fluorescent liposome was performed as follows: 400 μL of the liposome formulation was dissolved in 8 mL of HEPES 1× buffer. The polymer solution (210 μL) was hydrated and extruded as per the liposome formulation protocol, but without lipids and cholesterol. Then again 400 μL of this solution was dissolved in 8 mL of the buffer. 2.8 mL of the stock solution was placed in a 5-cm dialysis bag with a MWCO of 100 KDa (Spectrum™ labs, biotech, CE, dialysis kit, #08-700-131). The polymer and the liposome were dialyzed under gentle stirring against a solution of 0.9% NaCl for 120 hours, samples were collected inside the dialysis bag. The sample was protected from light during all the dialysis experiment. To ensure sink conditions, the dialysate was changed at each time point. The starting lipid concentration for the liposome was around 0.54 mM, determined by the phosphorous colorimetric assay.

(iv) Stability of the Liposomes

In order to understand if the incorporation of the CTA-PMGA-DODA (for polymer with n=45; M=6,500 g/mol) to liposomes can affect their stability in different conditions, we used a water-soluble fluorescent dye (HPTS) and encapsulated it with a proximity quencher (DPX) inside the aqueous cavity of the liposome. This system allows to monitor the disruption of the vesicles by a strong increase in fluorescence when the dye and the quencher are released in the surrounding environment. Liposomes hydrated with HEPES solution containing HPTS/DPX were purified by SEC on a 1×20 cm gravity flow column pack with Sephadex® G-25. Then, 10 μL of the purified liposomes suspensions were added to 1 mL of buffer, either HEPES pH=7.4 or 0.1 M citrate buffer pH=5.2 (0.063 M sodium citrate dihydrate and 0.037 M citric acid). The buffer with liposomes was incubated for 1 hour at 37° C. and 60° C. and the fluorescence was measured every 15 minutes. Triton X 20% (v/v) was added at the end (after 60 minutes) to measure the disruption of the liposome, resulting in the complete release of the dye ($\lambda_{ex/em}$: 413/512 nm).

(v) Cytotoxicity of the PMGA-liposome (for polymer with n=45; M=6,500 g/mol)

To measure the toxicity of the polymer we used MTT assays as follows: murine macrophage cells (RAW 264.7) were seeded at a concentration of 50 000 cells/wells in DMEM media with sodium pyruvate, 10% fetal bovine serum (FBS) and an antibiotic. The cells were incubated 24 hours at 37° C. with 5% $CO_2$ before further use. Liposome and free polymer solution were prepared in range of 0-20 μg quantity of material. 100 μL were added to the cell and left for 72 hours in the incubator. In the meantime, a solution of 3-(4,5-dimethylthiazoyl-2-yl)-2,5-diphenyl tetrazolium bromide salt (MTT) at a concentration of 5 mg/mL in sterile PBS was prepared. After incubation, 10 μL of the MTT solution was added in each well and incubated for 4 hours. The media was removed and replaced by 100 μL of dimethyl sulfoxide (DMSO). The absorbance was read at λ=570 nm.

Example 5—In Vitro Study

TABLE 3

Dynamic light scattering (DLS) size for all the formulation use for in vitro work

| Name | Size (nm) | PD |
|---|---|---|
| Control liposome for RAW 264.7 | 120.9 | 0.212 |
| PMGA-DODA$_{6.5k}$ liposome for RAW 264.7 | 116.4 | 0.237 |
| Control liposome for RAW 264.7 + GalNAc | 123.4 | 0.238 |
| PMGA-DODA$_{6.5k}$ liposome for RAW 264.7 + GalNAc | 120.2 | 0.124 |
| Control liposome for RAW 264.7 + Mannan | 113.6 | 0.246 |
| PMGA-DODA$_{6.5k}$ liposome for RAW 264.7 + Mannan | 110.4 | 0.186 |
| Control liposome A20 | 124.9 | 0.187 |
| PMGA-DODA$_{6.5k}$ liposome A20 | 110.3 | 0.234 |
| Control liposome dendritic cells | 108.8 | 0.260 |
| PMGA-DODA$_{6.5k}$ liposome dendritic cells | 121.9 | 0.189 |
| Control liposome MTT assay | 115.9 | 0.199 |
| PMGA-DODA$_{6.5k}$ liposome MTT assay | 114.9 | 0.076 |
| Control liposome U87 | 126.9 | 0.215 |
| PMGA-DODA$_{6.5k}$ liposome U87 | 116.1 | 0.133 |
| Control liposome A549 | 117.2 | 0.367 |
| PMGA-DODA$_{6.5k}$ liposome A549 | 125.4 | 0.132 |
| DSPE-PEG liposome A549 | 125.7 | 0.252 |

(i) Internalization with Macrophages Cells RAW 264.7

Uptake in different cells line: the liposomes were all formulated as previously described with DID' as a fluorophore reference for flow cytometry analysis. First, we use murine macrophages cells (RAW 264.7). About 550 000 cells were plated in each wells the night before with DMEM medium containing 10% FBS and an antibiotic. Solution of 0.1 and 0.025 mg/mL of liposomes were prepared. 10 μL of each solution was added into the wells and incubated for 2 hours. The cells were suspended by up and down pipetting, and the suspension was washed with PBS. Before Flow cytometry reading, the cells suspensions where centrifuged at 300 g for 5 minutes at 4° C., the medium were aspirated, and the cell pellets where resuspended 2 times in FACS buffer (2% FBS with 1 mM EDTA in PBS). Flow cytometry experiment (fluorescence-assisted cell sorting, FACS) was conducted on a BD LSRII (BD Biosciences) and the data were analyzed using the FlowJo V10 software (Tree Star Inc., BD) with the 640 nm laser (660/20 filter).

(ii) Internalization in Dendritic Cells

Primary mouse dendritic cells differentiated from bone narrow were seeded at a concentration of 200 000 cells/wells with DMEM medium (10% FBS and antibiotic). 10 μL of 0.1, 0.2, 0.5 and 1 mg/mL were added to the cells and incubated for 2 hours. The same process for cytometry analysis was used.

(iii) Internalization in B Cells

The same protocol was used to assess the internalization in B-cells derived from lymphoma old BALB/c mouse (A-20) with 500 000 cells/wells. The cell culture media was RPMI with glutamine and 10% FBS. The concentration of the solutions used were 0.5, 0.1 and 0.05 mg/mL. For adherent cells trypsin solution of 2.5% is required to detach the cells from the plate. 100 μL of the trypsin solution is added to the plate after washing the cells with PBS and incubated for 3-5 minutes at 37° C. Then a volume minimum of fresh media 5 times the trypsin is added to the plate before further washing and flow cytometry analysis. Experiments were also conducted on a glioblastoma cell line (U87-MG) and adenocarcinoma cells derived from primary lung tumors (A549) where 250 000 cells were plate in each well in EMEM medium (with Earle's salt, glutamine, 10% FBS and antibiotic) and DMEM respectively. The concentration of liposome used were 0.01 and 0.1 mg/mL for U87-MG, and 0.05, 0.1 and 0.5 mg/mL for A549 cells. 10 μL of each solution was added into the wells and the cells were incubated 2 hours and 4 hours respectively. Those cell lines are also adherent, which required the use of trypsin has mentioned before. The rest of the protocol was done has previously described.

Example 6—In Vivo Pharmacokinetics

All animal studies were conducted using approved protocols from Université Laval (Canadian Council on Animal Care standards and Animal Research: Reporting In Vivo Experiments Guidelines). Pharmacokinetic was carried according to method already published by our laboratory (*Journal of Controlled Release* 2018, 287, 121-131). Healthy animals were housed in a controlled environment (22° C., 12 hours day/night cycle) with ad libitum access to food and water. A total of 11 healthy male mice were divided in three groups (3-3-5). As a blank, liposomes without polymer on the surface were injected intravenously by the subclavian vein at a concentration of 2 mg/kg of phospholipids. Approximately 30-50 μL of blood was collected at various times (0.25, 0.5, 1, 2, 4, 6 Hours). Six hours post-injection, blood was collected by cardiac puncture for a terminal timepoint. Animals were euthanized by a cardiac perfusion with 3 mL of isotonic phosphate-buffered saline solution pH=7.2 (potassium phosphate 1.1 mmol/L, NaCl 150 mmol/L, disodium phosphate 3 mmol/L) and organs were collected. Biological samples were digested at 58° C. (in Solvable®, Perkin Elmer®), bleached with 30% hydrogen peroxide, and assessed by scintillation counting, using Hionic Fluor® (Perkin Elmer®) as a scintillation cocktail.

TABLE 4

Size and zeta potential of all liposome formulations used for in vivo study

| Name | Size (nm) | PD | Zeta potential (mV) |
|---|---|---|---|
| Control liposome HSPC/Cholesterol | 100.3 | 0.075 | −14.0 |
| Liposome CTA-PMGA-$DODA_{6.5k}$ | 122.6 | 0.142 | −5.65 |
| Liposome PMGA-$DODA_{6.5k}$ | 106 | 0.075 | −3.82 |

In order to analyse the cellular distribution into the spleen and the lymph node, control or PMGA liposomes (2 mg/kg) were injected into balb/c mice by subcutaneous hock injection. The spleen and the popliteal lymph node were collected 24 hours post-injection and placed in cold PBS with 2 vol % fetal bovine serum (FBS). Cellular suspension was prepared by mechanically disrupted the organs on a 40 μm cell strainer into a 6 wells plate containing 2 ml of PBS with 2% FBS on ice. Filtered cells were washed twice by centrifugation in 2 vol % FBS in PBS and counted on a hemocytometer. Erythrocytes were lysed by suspending the cells in Lysing Buffer (BD Biosciences) for 5 minutes. Then Saline buffer (PBS) were added and centrifuge. Cell suspensions of $5\times10^6$ cells/ml were labelled with antibodies mix and FC block (ThermoFisher). The panel of fluorophores and the reference numbers for antibodies are listed in Supplementary info. Control animals that had not received liposome were used to determine the background, and the positive signal for DiD' fluorophore.

TABLE 5

Biodistribution profile in the organs after i.v injection (2 mg/kg), n represents the number of mice.

| Time (h) | % ID per gram of blood<br>Control liposome (n = 6) | Liposome CTA-PMGA-$DODA_{6.5k}$ (n = 5) | Liposome PMGA-$DODA_{6.5k}$ (n = 5) |
|---|---|---|---|
| 0.25 | 25 ± 5 | 17 ± 2 | 17 ± 2 |
| 0.5 | 20 ± 5 | 12 ± 1 | 13 ± 1 |
| 1 | 16 ± 2 | 9 ± 2 | 11 ± 2 |
| 2 | 14 ± 3 | 8 ± 1 | 12 ± 2 |
| 4 | 12 ± 1 | 9 ± 1 | 11 ± 2 |
| 6 | 7 ± 1 | 8 ± 1 | 10 ± 1 |
| AUC (% ID h · $g^{-1}$) | 81 ± 11 | 54 ± 7 | 68 ± 9 |
| Kel ($h^{-1}$) | 0.38 ± 0.04 | 0.37 ± 0.07 | 0.31 ± 0.05 |

Figure 20:
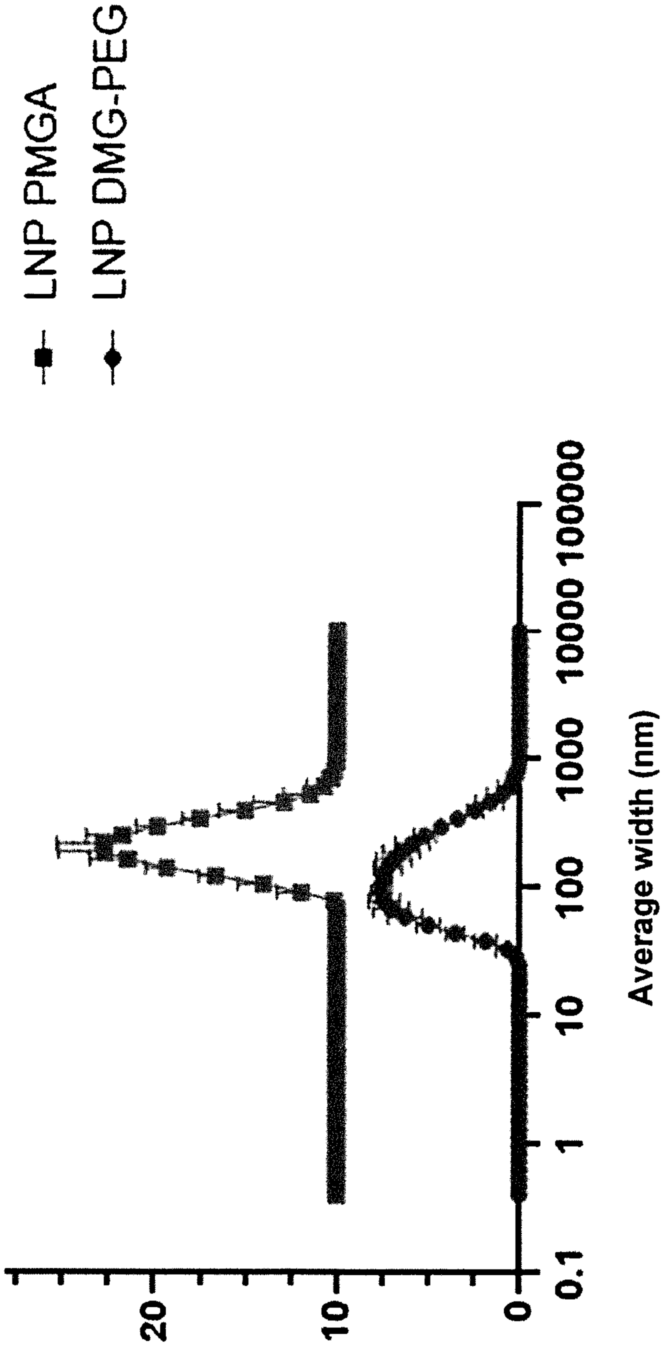
FIG. 20 shows the average diameter of the prepared PMGA-DODA LNP compared to DMG-LNP.

Example 7—Preparation of LNP with mRNA mRNA-containing lipid nanoparticles were formulated using the Spark™ Nanoassemblr (Precision Nanosystem). Ethanol solutions of the lipids (50 mM, 50 mol % SM-102, 10 mol % HSPC, 38.5 mol % Cholesterol and 1.5 mol % of PMGA-DODA (for polymer with n=45; M=6,500 g/mol)) were prepared, as well as a 0.464 mg/mL solution of GFP-encoding mRNA (Trilink) in 0.1M RNase free acetate buffer (pH=4, 0.02269 M sodium acetate, 0.07731M acetic acid). The mRNA concentration in the solution was assessed by UV-spectrophotometry (NanoDrop™ spectrophotometers, ThermoFisher). Each batch of nanoparticles was prepared using 12 μL of the lipid mix, and 24 μL of the mRNA solution (N/P=6). As per the Precision Nanosystem's protocol, these solutions were rapidly mixed and diluted in 36 μL of sterile PBS without $Ca^{2+}$ and $Mg^{2+}$. After formulation, the LNPs were further diluted in 72 μL of PBS. The efficacy of encapsulation was measured using the ribogreen assay (Invitrogen, Quant-it™, Ribogreen ARN assay kit, ThermoFisher #R11490). The LNP were diluted into 1×TE buffer (10 mmol/L Tris, 1 mmol/L EDTA) or 2% Triton buffer in TE solution. A calibration curve in TE buffer was set up using RNA stock solution prepared at 0.464 mg/mL (range between 2.5 and 0.1 ug/mL final concentration) to allow the quantification of free mRNA in the sample. The plate was incubated at 37° C. for 10 minutes to lyse the RNA-LNP in presence of Triton. 100 μL of the Ribogreen solution (1:100 Rigogreen reagent: TE buffer) was added in each well and the fluorescence was measured (λex/em: 485/528 nm) with Spectramax I3 (Molecular devices). The mRNA encapsulated was calculated by substracting the free mRNA to the LNP associated and comparing it to the calibration curve. The size of the LNP was confirmed by DLS (FIG. 20).

TABLE 6

Size and efficiency of mRNA encapsulation for LNP

| LNP | Size (nm) | PD | Encapsulation (%) |
|---|---|---|---|
| DMG-PEG | 147 | 0.306 | 92.4 |
| PMGA-$DODA_{6.5k}$ | 171.6 | 0.129 | 96.7 |

Example 8—Transfection

The human embryonic kidney immortalized cells (HEK293) were plate the day before the experiment at a concentration of 125 000 cells/wells. The DMEM media was replaced with reduced serum media the day of the transfection, such has optiMEM® (Gibco, #31985062). The LNP were diluted to 40,100 and 1000× and 20 μL of each solution were add to the cells and incubated for 24 hours at 37° C. with 5% $CO_2$. After transfection, the cells were trypsined has previously described and wash 2 times with FACS buffer. The transfection was analyzed by flow cytometry using the 488 nm laser (525/25 filter).

Example 9—Drug Loading

Liposomes with or without PMGA were prepared by the hydration of a lipid film with 100 mM citrate buffer (pH 4), followed by extrusion on polycarbonate membranes. The control and PMGA-containing formulations contained HSPC/Cholesterol at a 60:40 mol %, and HSPC/Cholesterol/PMGA at a 58:40:2 mol %, respectively. After hydration, formulations were extruded on polycarbonate membranes with pores ranging from 400-50 nm, to afford vesicles with hydrodynamic diameters between 90-130 nm. A transmembrane pH gradient was generated by exchanging the outside buffer with isotonic hepes buffer saline (HBS, pH 7.4, 22 mM HEPES, 147 mM NaCl) on a Sephadex G-25 column (1×20 cm). (Transmembrane pH-gradient liposomes to treat cardiovascular drug intoxication, *ACS Nano.,* 2010, 4, 7552). The concentration in liposomes was measured by the phosphate assay (Drinkable lecithin nanovesicles to study the biological effects of individual hydrophobic macronutrients and food preferences, *Food Chem.,* 2020, 322, 126736).

To load doxorubicin, a solution of doxorubicin HCl (5 mg/mL) was incubated with liposomes (HSPC liposomes:

0.0031 mmol/mL of phospholipid and HSPC-PMGA liposomes: 0.0024 mmol/mL) at a volume ratio of 0.3:1, for 18 hours at 37° C. The non-encapsulated doxorubicin was removed by size exclusion chromatography. The liposomes concentration was evaluated by the phosphate assay as above, and the doxorubicin concentration was measured by reverse-phase high performance chromatography (C18 4.6× 100 mm, with a gradient of pH 5 citric acid buffer and methanol). The doxorubicin (Retention time 4.37 min) was detected by UV absorbance (480 nm) and fluorescence spectroscopy (λex/Em: 480/490 nm). For both formulations, the process resulted in a drug loading of 14 wt %, showing that incorporation of PMGA in the liposome membrane does not compromise the remote loading of weakly basic molecules within the vesicles.

Example 10—In Vitro Study

The cytotoxicity of the formulations of Example 9 was evaluated in RAW 267.4 cells. One thousand eight hundred and fifty cells (1850 cells) cultivated in DMEM supplemented with 10% FBS were placed in 96 well plates, 24 hours before the experiment. These cells were then incubated with increasing quantities of doxorubicin for 2, 4, 8 and 24 hours, after which non-internalized liposomes were removed and replaced by fresh media. Cells were cultivated for a total of 48 hours, and cell viability was evaluated using the sulforhodamine B (SRB) assay. The range of doxorubicin concentrations tested were between 78 and 2.4 μM. For all incubation times, the IC50 of the doxorubicin encapsulated in PMGA-containing liposomes was between 1.3 and 2.9 times lower, than control liposomes without PMGA. This shows that the increased internalization observed previously translates into improved pharmacology of cytotoxic drugs.

Altogether, these experiments demonstrate that 1) the incorporation of PMGA in the liposome membrane does not compromise the ability of the vesicles as drug carriers, and 2) the incorporation of PMGA in the liposome membrane allows to potentiate the therapeutic activity of a model cytotoxic drug in vitro.

Although the invention has been illustrated and described with respect to one or more implementations, equivalent alterations and modifications will occur to others skilled in the art upon the reading and understanding of this specification. In addition, while a particular feature of the invention may have been disclosed with respect to only one of several implementations, such feature may be combined with one or more other features of the other implementations as may be desired and advantageous for any given or particular application.

Accordingly, it is understood that the examples and embodiments described herein are for illustrative purposes only and that various modifications or changes in light thereof will be suggested to persons skilled in the art and are to be included within the spirit and purview of this application and scope of the appended claims. Any publication, document, patent, patent application or publication referred to herein should be construed as incorporated by reference each in their entirety for all purposes.

The invention claimed is:

1. An amphiphilic poly(monoglycerol acrylate) (PMGA) polymer, comprising an hydrophilic repeating unit of monoglycerol acrylate; and one or more biodegradable hydrophobic group;

wherein the polymer is a comb polymer having an average molecular weight (Mw) ranging between 1000 and 15000, ranging between 1800 and 12000, of about 1800, of about 6500, or of about 12000;

wherein the Mw of the at least one biodegradable hydrophobic group represents at least 5%, at least 10%, at least 30%, between 5% and 30%, between 10% and 30%, about 5%, about 10% or about 30% of the average Mw of the polymer; and wherein the PMGA polymer is of Formula (I):

Formula I

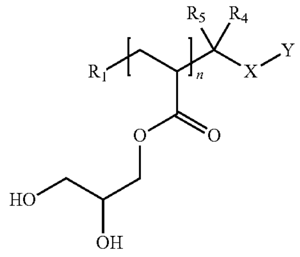

wherein n is an integer between 10 and 80, between 30 and 50, between 40 and 50, or about 42;

X is $—(CH_2)_m—$ with m between 0 and 4;

$R_1$ is a donor group or $R_1$ is halogen, —H, —OH, —SH, $—S(C{=}S)S—C_{6-10}$aryl, $—S(C{=}S)S—C_{1-24}$alkyl, $—S(C{=}S)C_{1-24}$alkyl, or —S(C=S)Ph;

Y is —OH, —COOH, $—OR_6$, $—COO(CH_2)_LNR_2R_3$ or $—CONR_2R_3$ with L between 1 and 18;

$R_2$ and $R_3$ are each independently —H, $C_{6-10}$aryl, $C_{3-12}$cycloalkyl, steroidyl groups, $C_{3-24}$alkyl, $C_{3-24}$alkenyl or $C_{3-24}$alkynyl;

$R_4$ and $R_5$ are each independently —H, $—CH_3$ or —CN; and $R_6$ is $(CH_2)_{L'}CH_3$, or $(CH_2)_{L'}NR_2R_3$ with L' between 0 and 18.

2. The polymer of formula (I) according to claim 1, wherein $R_2$ and $R_3$ are each independently linear $C_{6-24}$ alkyl.

3. The polymer of formula (I) according to claim 1, wherein $R_1$ is —SH.

4. The polymer of formula (I) according to claim 1, wherein n is comprised between 30 and 50.

5. The polymer of formula (I) according to claim 1, wherein $R_4$ is $—CH_3$ and $R_5$ is —CN.

6. The polymer of formula (I) according to claim 1, wherein X is $—CH_2CH_2—$ and Y is $—CONR_2R_3$.

7. The polymer of formula (I) according to claim 1, wherein $R_1$ is —SH, $R_4$ is $—CH_3$, $R_5$ is —CN, X is $—CH_2CH_2—$ and Y is $—CONR_2R_3$, wherein $R_2$ and $R_3$ are $C_{18}H_{37}$.

8. The polymer of formula (I) according to claim 1, wherein $R_1$ is $—S(C{=}S)S(CH_2)_{11}—CH_3$, $R_4$ is $—CH_3$, $R_5$ is —CN, X is $—CH_2CH_2—$ and Y is $—CONR_2R_3$, wherein $R_2$ and $R_3$ are $C_{18}H_{37}$.

9. The polymer of formula (I) according to claim 1, wherein $R_1$ is halogen, —H, —OH, —SH, $—S(C{=}S)S—C_{6-10}$aryl, $—S(C{=}S)S—C_{1-24}$alkyl, $—S(C{=}S)C_{1-24}$alkyl, or —S(C=S)Ph.

10. The polymer of formula (I) according to claim 1, wherein n is comprised between 10 and 50.

11. A lipid particle, wherein the lipid particle comprises:

an optional ionizable lipid;

a phosphatidyl choline;

a sterol; and an amphiphilic PMGA polymer as defined in claim 1.

12. The lipid particle of claim 11, wherein the ionizable lipid is SM-102, the phosphatidyl choline is HSPC and/or the sterol is cholesterol.

13. The lipid particle according to claim 11, wherein said particle is a lipid nanoparticle.

14. The lipid particle according to claim 13, wherein the lipid particle comprises molar ratios of 10% of HSPC, 50% of SM-102, 38.5% of cholesterol and 1.5% of the amphiphilic PMGA polymer.

15. The lipid particle according to claim 11, wherein said particle is a liposome optionally comprising a bioactive agent.

16. The lipid particle according to claim 15, wherein the lipid particle comprises molar ratios of about 58% of SM-102 and HSPC, 40% of cholesterol and 2% of the amphiphilic PMGA polymer.

17. The lipid nanoparticle according to claim 15, further wherein the bioactive agent is a drug, or a nucleic acid selected from the group consisting of mRNA, siRNA, shRNA and microRNA.

18. A pharmaceutical composition comprising the lipid particle according to claim 11, and a pharmaceutically acceptable excipient, carrier, or diluent.

19. A method of preparing an amphiphilic PMGA polymer as defined in claim 1, said method comprising:

- providing a monoglycerol acrylate monomer, radically polymerizable monomer;
- providing a chain transfer agent; and
- polymerizing the monomer via reversible addition-fragmentation chain-transfer polymerization (RAFT), in the presence of a free radical initiator and the chain transfer agent, wherein said polymerization is carried out in conditions allowing to obtain a polymer incorporating at least 10 monomer units (n), and
- wherein the method optionally further comprises the removal of thiocarbonylthio end groups by chemical reaction.

20. The method according to claim 19, wherein radically polymerizable monomer is monoglycerol acrylate and/or the chain transfer agent is selected from the group consisting of:

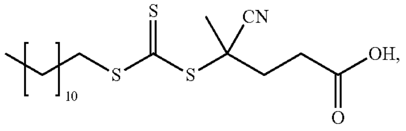

-continued

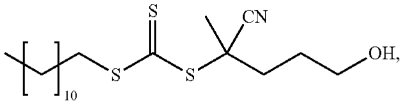

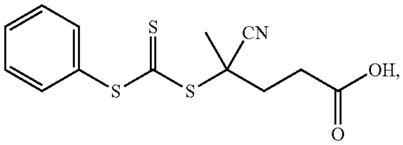

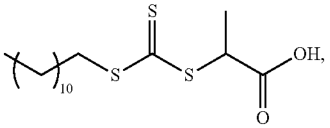

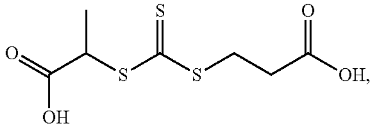

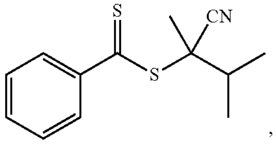

,

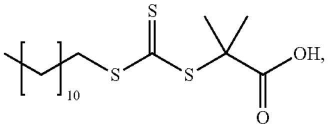

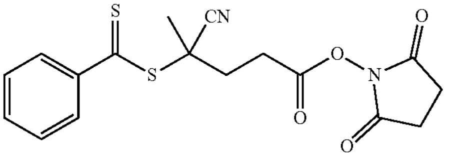

and

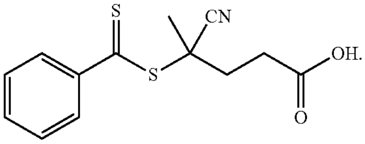

* * * * *